US012751470B2

(12) United States Patent
Siankevich et al.

(10) Patent No.: US 12,751,470 B2
(45) Date of Patent: Oct. 6, 2026

(54) USE OF IONIC POLYMERS IN BIOMASS PROCESSING FOR PREPARATION OF ANIMAL FEED ADDITIVE

(71) Applicant: EMBION TECHNOLOGIES SA, Etoy (CH)

(72) Inventors: Sviatlana Siankevich, Fechy (CH); Georgios Savoglidis, Fechy (CH)

(73) Assignee: EMBION TECHNOLOGIES SA, Etoy (CH)

( * ) Notice: Subject to any disclaimer, the term of this patent is extended or adjusted under 35 U.S.C. 154(b) by 1020 days.

(21) Appl. No.: 17/796,943

(22) PCT Filed: Feb. 4, 2021

(86) PCT No.: PCT/EP2021/052598
§ 371 (c)(1),
(2) Date: Aug. 2, 2022

(87) PCT Pub. No.: WO2021/156332
PCT Pub. Date: Aug. 12, 2021

(65) Prior Publication Data

US 2023/0101104 A1 Mar. 30, 2023

(30) Foreign Application Priority Data

Feb. 4, 2020 (EP) .................................... 20155424

(51) Int. Cl.

*A23K 20/147* (2016.01)
*A23K 10/38* (2016.01)
*A23K 20/163* (2016.01)
*A23K 50/75* (2016.01)
*A61K 31/702* (2006.01)
*A61K 38/01* (2006.01)
*A61P 3/02* (2006.01)
*A61P 3/04* (2006.01)

(52) U.S. Cl.
CPC ............ *A23K 20/147* (2016.05); *A23K 10/38* (2016.05); *A23K 20/163* (2016.05); *A23K 50/75* (2016.05); *A61K 31/702* (2013.01); *A61K 38/01* (2013.01); *A61P 3/02* (2018.01); *A61P 3/04* (2018.01)

(58) Field of Classification Search
CPC .... A23K 20/147; A23K 20/163; A23K 50/75; A23K 10/38; A61P 3/02; A61P 3/04; A61K 31/05; A61K 31/702; A61K 38/01
USPC .......................................................... 536/4.1
See application file for complete search history.

(56) References Cited

U.S. PATENT DOCUMENTS 8,030,030 B2 10/2011 Varanasi et al.
8,575,374 B1 11/2013 DeLong et al.
10,894,851 B2 1/2021 Dyson et al.
11,925,925 B2 * 3/2024 Siankevich .............. B01J 31/08
2002/0028887 A1 3/2002 Hirano et al.
2010/0319862 A1 12/2010 Rahman
2011/0020498 A1 1/2011 Broekaert et al.
2014/0378412 A1 12/2014 Lowe et al.
2016/0032038 A1 2/2016 Baynes et al.
2020/0246785 A1 8/2020 Siankevich et al.
2023/0098502 A1 3/2023 Siankevich et al.
2025/0134800 A1 5/2025 Siankevich et al.

FOREIGN PATENT DOCUMENTS

CN 106632164 A 5/2017
KR 2014 0114316 A 9/2014
WO WO-2006053083 A2 5/2006
WO WO-2009114830 A2 9/2009
WO 2011073437 A2 6/2011
WO WO-2013066941 A1 5/2013
WO WO-2017158117 A1 9/2017
WO WO-2019 058270 A1 3/2019
WO WO-2021156331 A2 8/2021

OTHER PUBLICATIONS

Courtin et al., "Dietary Inclusion of Wheat Bran Arabinoxylooligosaccharides Induces Beneficial Nutritional Effects in Chickens", Cereal Chemistry 85 (5) pp. 607-613 (2009).
International Search Report from PCT Application No. PCT/EP2021/052598 dated May 7, 2021.
Written Opinion from PCT Application No. PCT/EP2021/052598 dated May 7, 2021.
Pourjavadi, A., et al., "Crosslinked poly(ionic liquid) as high loaded dual acidic organocatalyst," Journal of Molecular Catalysis A: Chemical, 365: 55-59 (2012).
International Search Report from corresponding PCT Application No. PCT/IB2018/057206 dated Mar. 28, 2019.
Written Opinion from corresponding PCT Application No. PCT/IB2018/057206 dated Mar. 28, 2019.
Office Action from corresponding U.S. Appl. No. 16/648,351 dated May 10, 2022.
Office Action from corresponding U.S. Appl. No. 16/648,351 dated Jan. 24, 2022.
Xu et al., "Trypsin entrapped in poly (diallyldimethylammonium chloride) silica sol-gel microreactor coupled to matrix-assisted laser desorption/ionization time-of-flight mass spectrometry," Rapid Communications in Mass Spectrometry, (22) pp. 1257-1264 (2008).
Hyun et al., "Utilization of bovine blood plasma proteins for the production of angiotensin I converting enzyme inhibitory peptides," Process Biochemistry (36) pp. 65-71 (2000).
International Search Report from PCT Application No. PCT/EP2021/052597 dated Aug. 9, 2021.
Written Opinion from PCT Application No. PCT/EP2021/052597 dated Aug. 9, 2021.
U.S. Appl. No. 17/796,947, filed Aug. 2, 2022.

(Continued)

*Primary Examiner* — Yih-Horng Shiao
(74) *Attorney, Agent, or Firm* — Harness Dickey & Pierce P.L.C.

(57) ABSTRACT

The invention relates to an animal feed additive comprising oligosaccharides, proteins, lipids, phenolic compounds and minerals, wherein the oligosaccharides comprise glucans, xylans, arabinans and mannans, and wherein degree of polymerisation (DP) of the oligosaccharides is DP1 to DP30 and to a method for preparing thereof from biomass.

2 Claims, 3 Drawing Sheets

(56) References Cited

OTHER PUBLICATIONS

U.S. Appl. No. 16/648,351, filed Mar. 18, 2020.
International Search Report and Written Opinion from PCT Application No. PCT/EP2023/052605 dated Apr. 13, 2023.

* cited by examiner

USE OF IONIC POLYMERS IN BIOMASS PROCESSING FOR PREPARATION OF ANIMAL FEED ADDITIVE

PRIORITY STATEMENT

This application is a national stage application under 35 U.S.C. § 371 of PCT International Application No. PCT/EP2021/052598, which has an international filing date of 4 Feb. 2021 and claims priority under 35 U.S.C. § 119 to European Patent Application No. 20155424.3 filed on 4 Feb. 2020. The contents of each application recited above are incorporated herein by reference in their entirety.

FIELD OF THE INVENTION

The invention relates to an animal feed additive comprising oligosaccharides, proteins, lipids, phenolic compounds and minerals, wherein the oligosaccharides comprise glucans, xylans, arabinans and mannans, and wherein degree of polymerisation (DP) of the oligosaccharides is DP1 to DP30 and to a method for preparing thereof from biomass.

BACKGROUND OF THE INVENTION

The use of antibiotics as a growth and health promoter by adding the antibiotics to animal feed is well known. However, due to concerns regarding the use of such compounds, in particular, concerns about the residues from using such compounds and their implication in the development of antibiotic-resistant bacteria, there is still a need to provide alternative strategies and alternative animal feed additives.

SUMMARY OF THE INVENTION

An aspect of the present invention provides an animal feed additive comprising oligosaccharides, proteins, lipids, phenolic compounds and minerals, wherein the oligosaccharides are selected from the group comprising glucans, xylans, arabinans and/or mannans, and wherein degree of polymerisation (DP) of the oligosaccharides is DP1 to DP30.

Another aspect of the present invention provides an animal feed composition comprising an animal foodstuff and/or a basic animal diet formula and an effective amount of the animal feed additive of the invention.

Another aspect of the present invention provides a method of feeding an animal comprising feeding a monogastric animal with the animal feed composition of the invention or the animal feed additive of the invention.

Another aspect of the present invention provides a method of increasing weight gain in an animal, comprising feeding said animal with the animal feed composition of the invention or the animal feed additive of the invention.

Another aspect of the present invention provides a method for producing the animal feed additive of the invention, the method comprising the steps of:

a) providing biomass;

b) optionally determining lipids, proteins and/or carbohydrates contents in the biomass;

c) optionally pre-treating the biomass;

d) optionally removing lipids and/or proteins from the biomass;

e) contacting the biomass with a catalyst to form a reaction mixture, wherein the catalyst is an ionic polymer or a combination of ionic polymers, the ionic polymer network, a solid-supported ionic polymers and/or a polymer membrane incorporating ionic polymers;

f) degrading the biomass in the reaction mixture to produce a liquid phase and a solid phase, wherein the liquid phase includes the animal feed additive, and the solid phase includes residual biomass;

g) isolating at least a portion of the liquid phase from the solid phase; and h) recovering the animal feed additive from the isolated liquid phase.

wherein the ionic polymer (IP) consists of a monomer of formula I formula I

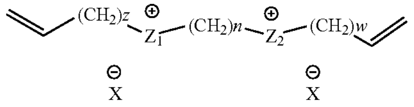

or consists of a first monomer of formula I formula I

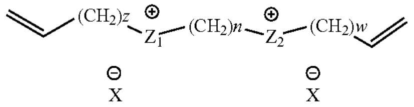

and at least one second monomer selected from the group consisting of formula II

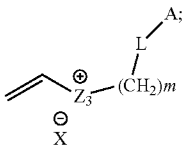

formula III

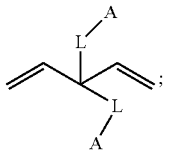

formula IV

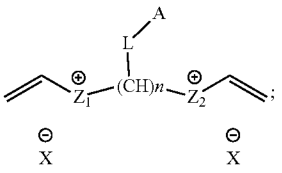

formula V

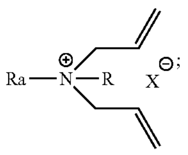

-continued formula VI

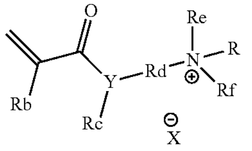

wherein n and m are independently selected from 1, 2, 3, 4, 5, 6;

z and w are independently selected from 0, 1, 2, 3;

$Z_1$, $Z_2$ and $Z_3$ are cations each independently selected from the group comprising:

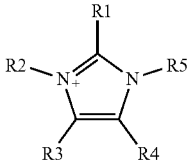
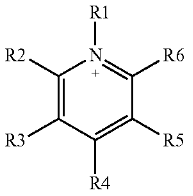
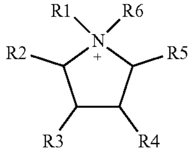
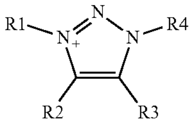
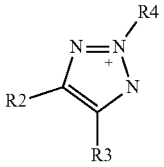
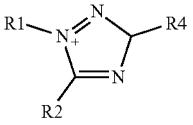
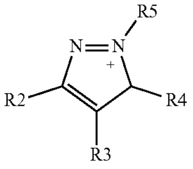
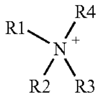
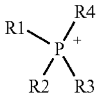
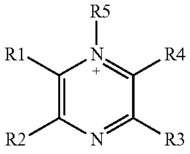
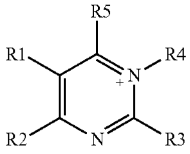
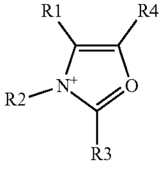
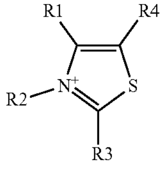
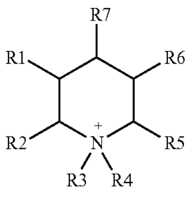
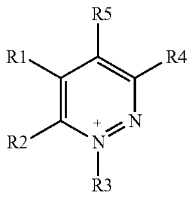

-continued

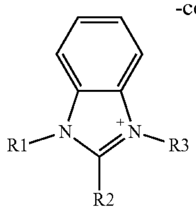
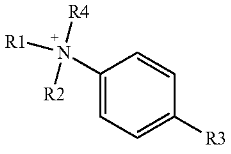

R1, R2, R3, R4, R5, R6 and R7 are each independently selected from the group comprising a bond, H, $C_1$-$C_6$ alkyl, $C_1$-$C_6$ allyl, $CH_3$—$(CH_2)$p-O—$(CH_2)$q-$CH_3$, $C_1$-$C_6$ alkoxy, $C_1$-$C_6$ alkoxyalkyl, benzyl, —$SO_3H$, —$(CH_2)$q-$SO_3H$, provided that two of R1, R2, R3, R4, R5, R6 and R7 are each a bond;

p and q are independently selected from 0, 1, 2, 3, 4, 5, 6;

L is an optional linker and each occurrence of L, if present, is independently selected from H, substituted or unsubstituted $C_1$-$C_{20}$ alkylene, alkenylene, alkynylene and substituted or unsubstituted $C_5$-$C_{10}$ aryl, wherein the substituents are selected from the group comprising H, —$SO_3H$, —COOH, —[P(═O)$(OH)_2$], —[P(═O)(OH)], —O—$SO_3H$, —O—COOH, —O—[P(═O)$(OH)_2$], —O—[P(═O)(OH)];

A is an optional acidic group and each occurrence of A, if present, is independently selected from the group comprising H, —$SO_3H$, —COOH, —[P(═O)$(OH)_2$], —[P(═O)(OH)], —O—$SO_3H$, —O—COOH, —O—[P(═O)$(OH)_2$], —O—[P(═O)(OH)], —$CH_2$—COOH, provided that when z and w are 0, A is present in formula IV;

$X^-$ is selected from the group comprising $F^-$, $Cl^-$, $Br^-$, $I^-$, $ClO_4^-$, $BF_4^-$, $PF_6^-$, $AsF_6^-$, $SbF_6^-$, $NO_2^-$, $NO_3^-$, $HSO_4^-$, $SO_4^{2-}$, $PO_4^{3-}$, $HPO_4^{2-}$, $CF_3CO_2^-$, $CF_3CO_3^-$, $CO_3^{2-}$, $CF_3SO_3^-$, $C_1$-$C_6$ carboxylate, $CN^-$, $SCN^-$, $OCN^-$, $CNO^-$, $N_3^-$, tosylate, mesylate, trifluoromethanesulfonate, trifluoroethane sulfonate, di-trifluoromethanesulfonyl amino, docusate, xylenesulfonate;

Ra is $C_1$-$C_{24}$ alkyl;

Rb and Rc are each independently selected from the group comprising H and $CH_3$ or absent;

Rd is $C_1$-$C_{24}$ alkylene or $C_1$-$C_{24}$ alkyl, optionally substituted by $C_1$-$C_{24}$ alkyl;

Re and Rf are each independently $C_1$-$C_{24}$ alkyl;

Y is N or O, provided that when Y is O, Rc is absent;

R is selected from the group comprising $C_1$-$C_{24}$ alkyl and $C_5$-$C_{10}$ aryl or is absent;

wherein the ionic polymer network comprises cross-linked the one or more ionic polymers (IP);

wherein the solid support has at least one surface comprising the one or more ionic polymers (IP) or the ionic polymer network;

wherein the polymer membrane incorporates the one or more ionic polymers (IP) or the ionic polymer network.

Another aspect of the present invention provides a ionic polymer (IP) consisting of a first monomer of formula I formula I

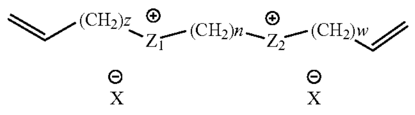

and at least one second monomer selected from the group consisting of formula II

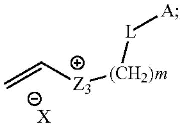

formula III

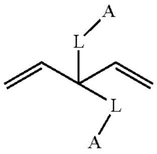

;

formula IV

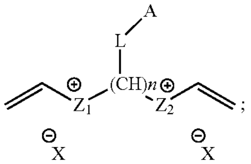

formula V

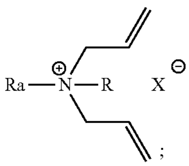

formula VI

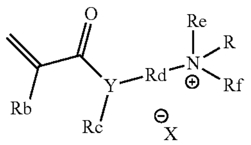

provided that at least the second monomer of formula V or at least the second monomer of formula VI is present in the ionic polymer (IP), wherein n and m are independently selected from 1, 2, 3, 4, 5, 6;

z and w are independently selected from 0, 1, 2, 3;

$Z_1$, $Z_2$ and $Z_3$ are cations each independently selected from the group comprising:

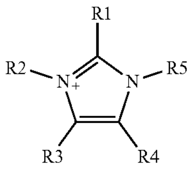

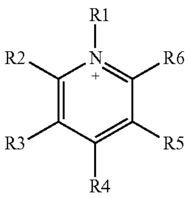

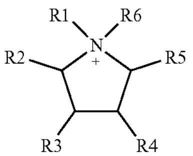

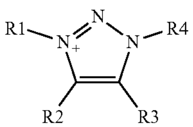

-continued

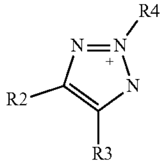

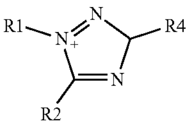

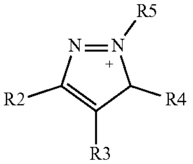

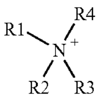

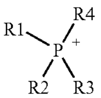

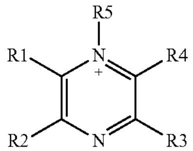

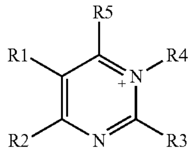

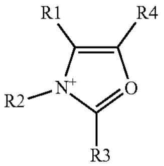

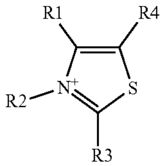

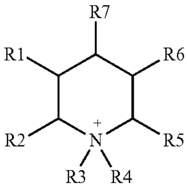

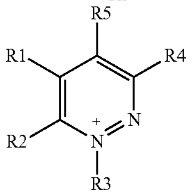

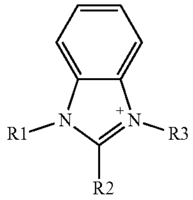

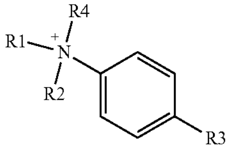

R1, R2, R3, R4, R5, R6 and R7 are each independently selected from the group comprising a bond, H, $C_1$-$C_6$ alkyl, $C_1$-$C_6$ allyl, $CH_3$—$(CH_2)$p-O—$(CH_2)$q-$CH_3$, $C_1$-$C_6$ alkoxy, $C_1$-$C_6$ alkoxyalkyl, benzyl, —$SO_3H$, —$(CH_2)$q-$SO_3H$, provided that two of R1, R2, R3, R4, R5, R6 and R7 are each a bond;

p and q are independently selected from 0, 1, 2, 3, 4, 5, 6;

L is an optional linker and each occurrence of L, if present, is independently selected from H, substituted or unsubstituted $C_1$-$C_{20}$ alkylene, $C_1$-$C_{20}$ alkenylene, $C_1$-$C_{20}$ alkynylene and substituted or unsubstituted $C_5$-$C_{10}$ aryl, wherein the substituents are selected from the group comprising H, —$SO_3H$, —COOH, —[P(═O)$(OH)_2$], —[P(═O)(OH)], —O—$SO_3H$, —O—COOH, —O—[P(═O)$(OH)_2$], —O—[P(═O)(OH)];

A is an optional acidic group and each occurrence of A, if present, is independently selected from the group comprising H, —$SO_3H$, —COOH, —[P(═O)$(OH)_2$], —[P(═O)(OH)], —O—$SO_3H$, —O—COOH, —O—[P(═O)$(OH)_2$], —O—[P(═O)(OH)], —$CH_2$—COOH, provided that when z and w are 0, A is present in formula IV;

$X^-$ is selected from the group comprising $F^-$, $Cl^-$, $Br^-$, $I^-$, $ClO_4^-$, $BF_4^-$, $PF_6^-$, $AsF_6^-$, $SbF_6^-$, $NO_2^-$, $NO_3^-$, $HSO_4^-$, $SO_4^{2-}$, $PO_4^{3-}$, $HPO_4^{2-}$, $CF_3CO_2^-$, $CF_3CO_3^-$, $CO_3^{2-}$, $CF_3SO_3^-$, $C_1$-$C_6$ carboxylate, $CN^-$, $SCN^-$, $OCN^-$, $CNO^-$, $N_3^-$, tosylate, mesylate, trifluoromethanesulfonate, trifluoroethane sulfonate, di-trifluoromethanesulfonyl amino, docusate, xylenesulfonate;

Ra is $C_1$-$C_{24}$ alkyl;

Rb and Rc are each independently selected from the group comprising H and $CH_3$ or absent;

Rd is $C_1$-$C_{24}$ alkylene or $C_1$-$C_{24}$ alkyl, optionally substituted by $C_1$-$C_{24}$ alkyl;

Re and Rf are each independently $C_1$-$C_{24}$ alkyl;

Y is N or O, provided that when Y is O, Rc is absent;

R is selected from the group comprising $C_1$-$C_{24}$ alkyl and $C_5$-$C_{10}$ aryl or is absent.

DETAILED DESCRIPTION OF THE INVENTION

Figure 1:
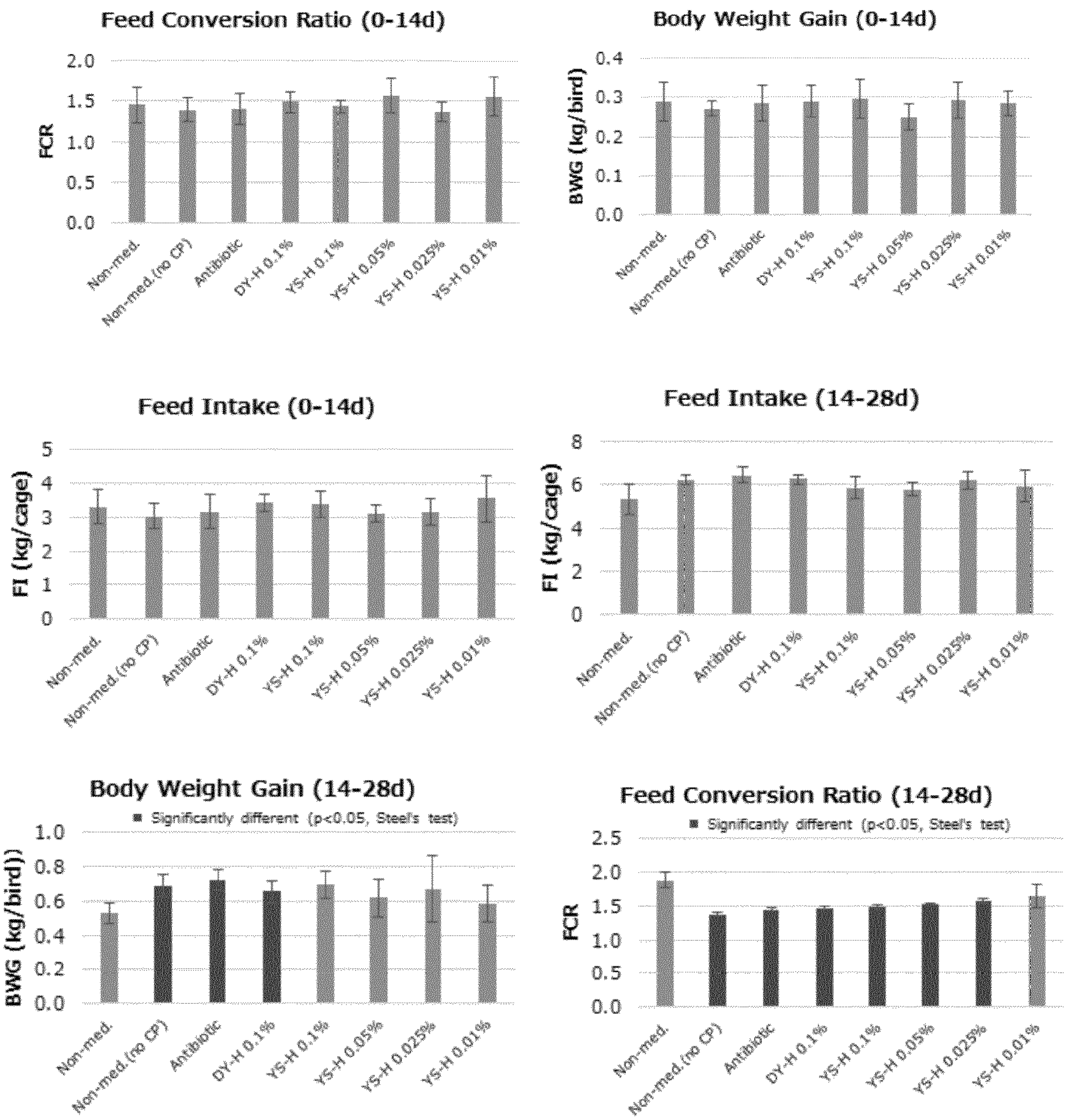
FIG. 1 shows animal performance on different treatments.

All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

In the case of conflict, the present specification, including definitions, will control. Unless defined otherwise, all technical and scientific terms used herein have the same meaning as is commonly understood by one of skill in art to which the subject matter herein belongs. As used herein, the following definitions are supplied in order to facilitate the understanding of the present invention.

The term "comprise" is generally used in the sense of include, that is to say permitting the presence of one or more features or components. Also as used in the specification and claims, the language "comprising" can include analogous embodiments described in terms of "consisting of" and/or "consisting essentially of".

As used in the specification and claims, the singular form "a", "an" and "the" include plural references unless the context clearly dictates otherwise.

As used in the specification and claims, the term "and/or" used in a phrase such as "A and/or B" herein is intended to include "A and B", "A or B", "A", and "B".

An "allyl" group is a substituent with the structural formula $H_2C{=}CH{-}CH_2R$, where R is the rest of the molecule.

The term "monomer" refers to a molecule that can undergo polymerization or copolymerization thereby contributing constitutional units to the essential structure of a macromolecule (a polymer).

"Cross-linking", as used herein, refers to the attachment of two or more monomers, oligomers or longer polymer chains by bridges of a cross-linker, such as an element, molecular group, a compound, or another oligomer or polymer. Cross-linking can result in a polymeric network (which can be two-dimensional or three-dimensional) where the polymer subunits are interconnected with multiple cross-linking agents and without free ends. Cross-linking may take place upon exposure to a stimulus, such as heat or light. As a result, some cross-linking processes occur at increased temperature, and some may also occur at room temperature or at lower temperature. As cross-linking density is increased, the properties of a material can be changed from thermoplastic to thermosetting.

The term "animal" as used herein refers to animals typically kept in farms, animal operations, zoos, and includes bovine, fowl, porcine, ovine, aquatic and equine species. Preferably "animal" is poultry, such as chickens, turkeys, ducks, quail, geese.

As used herein, the term "feed" broadly refers to any kind of material, liquid or solid, that is used for nourishing an animal, and for sustaining normal or accelerated growth of an animal including newborns and young developing animals.

A "feed additive" composition refers to a composition suitable for incorporation into the diet of an animal through incorporation into the animal's food and/or water.

As used herein, "phenolic compounds" are a group of small molecules characterized by their structures having at least one phenol unit.

As used herein, "animal performance" may be determined by the feed efficiency and/or weight gain of the animal and/or by the feed conversion ratio and/or by the digestibility of a nutrient in a feed (e.g. amino acid digestibility) and/or digestible energy or metabolizable energy in a feed and/or by nitrogen retention. Preferably "animal performance" is determined by feed efficiency and/or weight gain of the animal and/or by the feed conversion ratio.

By "improved animal performance" it is meant that there is increased feed efficiency, and/or increased weight gain and/or reduced feed conversion ratio and/or improved digestibility of nutrients or energy in a feed and/or by improved nitrogen retention resulting from the use of the animal feed additive of the invention in feed in comparison to feed which does not comprise said animal feed additive. Preferably, by "improved animal performance" it is meant that there is increased feed efficiency and/or increased weight gain and/or reduced feed conversion ratio.

As used herein, the term "feed efficiency" refers to the amount of weight gain in an animal that occurs when the animal is fed ad-libitum or a specified amount of food during a period of time.

By "increased feed efficiency" it is meant that the use of the animal feed additive according the invention in feed results in an increased weight gain per unit of feed intake compared with an animal fed without said animal feed additive being present.

As used herein, the term "feed conversion ratio" (FCR) refers to the amount of feed fed to an animal to increase the weight of the animal by a specified amount. An improved feed conversion ratio means a lower feed conversion ratio. By "lower feed conversion ratio" or "improved feed conversion ratio" it is meant that the use of the animal feed additive in feed results in a lower amount of feed being required to be fed to an animal to increase the weight of the animal by a specified amount compared to the amount of feed required to increase the weight of the animal by the same amount when the feed does not comprise said animal feed additive.

"Digestibility" or "nutrient digestibility" as used herein means the fraction of a nutrient that disappears from the gastro-intestinal tract or a specified segment of the gastro-intestinal tract, e.g. the small intestine. Nutrient digestibility may be measured as the difference between what is administered to the subject and what comes out in the faeces of the subject, or between what is administered to the subject and what remains in the digesta on a specified segment of the gastro intestinal trace, e.g. the ileum. Nutrient digestibility as used herein may be measured by the difference between the intake of a nutrient and the excreted nutrient by means of the total collection of excreta during a period of time; or with the use of an inert marker that is not absorbed by the animal, and allows the researcher calculating the amount of nutrient that disappeared in the entire gastro-intestinal tract or a segment of the gastro-intestinal tract. Such an inert marker may be titanium dioxide, chromic oxide or acid insoluble ash. Digestibility may be expressed as a percentage of the nutrient in the feed, or as mass units of digestible nutrient per mass units of nutrient in the feed. Nutrient digestibility as used herein encompasses starch digestibility, fat digestibility, protein digestibility, and amino acid digestibility.

"Energy digestibility" (or digestible energy) as used herein means the gross energy of the feed consumed minus the gross energy of the faeces or the gross energy of the feed consumed minus the gross energy of the remaining digesta on a specified segment of the gastro-intestinal tract of the animal, e.g. the ileum. "Metabolizable energy" as used herein refers to apparent metabolizable energy and means the gross energy of the feed consumed minus the gross energy contained in the faeces, urine, and gaseous products of digestion. Energy digestibility and metabolizable energy may be measured as the difference between the intake of gross energy and the gross energy excreted in the faeces or the digesta present in specified segment of the gastro-intestinal tract using the same methods to measure the digestibility of nutrients, with appropriate corrections for nitrogen excretion to calculate metabolizable energy of feed.

An "increased weight gain" refers to an animal having increased body weight on being fed feed comprising the animal feed additive compared with an animal being fed a feed without said animal feed additive being present.

Lesion scoring is a criterion for determining the pathogenicity of infectious species. "0" refers to normal, "1" refers to slight mucus covering small intestine, "2" refers to necrotic small intestine mucosa, "3" refers to sloughed and blood small intestine mucosa and contents.

An aspect of the present invention provides an animal feed additive suitable for feeding monogastric animals, in particular for poultries. The animal feed additive of the invention comprises oligosaccharides, proteins and/or protein hydrolysates, lipids, phenolic compounds and minerals, wherein the oligosaccharides are selected from the group comprising glucans, xylans, arabinans and/or mannans, and wherein degree of polymerisation (DP) of the oligosaccharides is DP1 to DP30.

In one embodiment, the animal feed additive of the invention consists of oligosaccharides, proteins, lipids, phenolic compounds, minerals and moisture, wherein the oligosaccharides are selected from the group comprising glucans, xylans, arabinans and/or mannans, and wherein degree of polymerisation (DP) of the oligosaccharides is DP1 to DP30.

According to an embodiment of the invention, the animal feed additive comprises (in wt %)

Total oligosaccharides: 25% to 100%, preferably 25% to 95% or 25% to 75%

Proteins and/or protein hydrolysates: 0% to 55%, preferably 5% to 55% or 10% to 55%

Lipids: 0% to 5%, preferably 0.5% to 2%

Phenolic compounds: 0% to 55%, preferably 2.5% to 55%

Minerals: <10%, preferably 0% to 4%, preferably 2.5% to 4%

Moisture: <10%, preferably <5% or 0% to 5% wherein the oligosaccharides are selected from the group comprising

Glucans: 0% to 40%, preferably 3% to 40%, by weight of total oligosaccharides

Xylans: 0% to 50%, preferably 10% to 50%, by weight of total oligosaccharides

Arabinans: 0% to 50%, preferably 0% to 40%, preferably 3% to 40%, by weight of total oligosaccharides Mannans: 0% to 30%, preferably 2% to 30%, by weight of total oligosaccharides and wherein distribution of degree of polymerisation (DP) of said oligosaccharides is DP1: 0% to 30%, preferably 1% to 30%

DP2 to DP30: >70%, preferably 70% to 75% or 70% to 100%.

According to another embodiment of the invention, the animal feed additive consists of (in wt 0%)

Total oligosaccharides: 25% to 100%, preferably 25% to 95% or 25% to 75%

Proteins and/or protein hydrolysates: 0% to 55%, preferably 5% to 55% or 10% to 55%

Lipids: 0% to 5%, preferably 0.5% to 2%

Phenolic compounds: 0% to 55%, preferably 2.5% to 55%

Minerals: <10%, preferably 0% to 4%, preferably 2.5% to 4%

Moisture: <10%, preferably <5% or 0% to 5% wherein the oligosaccharides are selected from the group comprising

Glucans: 0% to 40%, preferably 3% to 40%, by weight of total oligosaccharides

Xylans: 0% to 50%, preferably 10% to 50%, by weight of total oligosaccharides

Arabinans: 0% to 50%, preferably 0% to 40%, preferably 3% to 40%, by weight of total oligosaccharides Mannans: 0% to 30%, preferably 2% to 30%, by weight of total oligosaccharides and wherein distribution of degree of polymerisation (DP) of said oligosaccharides is DP1: 0% to 30%, preferably 1% to 30%

DP2 to DP30: >70%, preferably 70% to 75% or 70% to 100%.

Glucans, xylans, arabinans and mannans are major oligosaccharides present in the animal feed additive of the invention. Other oligosaccharides can be also present in the animal feed additive of the invention.

A particular embodiment provides the animal feed additive of the invention, wherein oligosaccharides comprise β-(1,4)-linked xylose units, β-(1,4)-linked xylose units substituted with α-(1,3) arabinose, linked glucose units forming (1,3)-(1,4)-β-D-glucan molecules.

Another particular embodiment provides the animal feed additive of the invention, wherein oligosaccharides comprise arabinoxylo-oligosaccharides, both linear and branched in their structure, preferably with at least one arabinose or xylose positioned at the reducing end of the oligosaccharide backbone.

The ratio between arabinose and xylose units in oligosaccharides varies depending on the reaction conditions and ionic polymer applied. Thus in one embodiment, in the animal feed additive of the invention the branched oligosaccharides comprise arabinose and xylose units, preferably with an arabinose/xylose ratio of 0.4-1.2, preferably a ratio of 0.4-1.0, preferably a ratio of 0.45-1.0, preferably a ratio of 0.5-0.9. In one embodiment of the animal feed additive of the invention, the branched or linear oligosaccharides comprise xylose units and practically free of arabinosyl groups.

In one embodiment, the oligosaccharides and/or the proteins in the animal feed additive of the invention have an average molecular weight less than 10 kDa, preferably less than 7.5 kDa, preferably less than 5 kDa, preferably less than 4 kDa, preferably less than 2 kDa.

In one embodiment of the animal feed additive of the invention, the oligosaccharides comprise at least two (β1-4) linked glucose unit linked together.

In one embodiment of the animal feed additive of the invention, the oligosaccharides comprise at least two (β1-4) linked xylose unit linked together.

In one embodiment of the animal feed additive of the invention, the oligosaccharides comprise at least one branch consisting of a (1-3) linked arabinose unit or (1-4) linked xylose unit linked to the backbone.

In one embodiment of the animal feed additive of the invention, the oligosaccharides comprise disaccharides and said disaccharides are linked with a (1-3) linkage between two xylose units or one arabinose and xylose unit.

In one embodiment of the animal feed additive of the invention, the oligosaccharides comprise at least one trisaccharide, wherein xylose is linked with a (1-4) linkage between two glucose units (Glc(α1-4)Xyl(α1-4)Glc) or one arabinose and xylose unit (Ara(α1-6)[Xyl(β1-4)]Glc).

In one embodiment of the animal feed additive of the invention, the oligosaccharides comprise at least one disaccharide linked with glucuronic acid (Ara(aα1-3)Xyl(β 1-2)] GlcA or GlcA(α1-2)Xyl(β 1-4)Xyl).

In one embodiment of the animal feed additive of the invention, the oligosaccharides comprise at least one xylose unit or xylose and arabinose linked with galactose or rhamnose and glucuronic acid (Xyl(β 1-3)[Gal(β 1-2)]GlcA and Xyl(β 1-4)Xyl(β 1-3)Rha(α1-2)GalA or Xyl(β 1-2)Ara(α1-3)[Gal(β 1-2)]GlcA).

In one embodiment of the animal feed additive of the invention, the oligosaccharides comprise at least one xylose or arabinose unit that can be substituted with O-acetyl- and 4-O-methylglucuronic acid groups.

In one embodiment of the animal feed additive of the invention, the oligosaccharides comprise at least two (α1-2) linked mannose units linked together.

In one embodiment of the animal feed additive of the invention, the oligosaccharides comprise at least one mannose unit linked with (α1-3) to at least two (α1-2) linked mannose units linked together (Man(α1-3)Man(α1-2)Man).

In one embodiment of the animal feed additive of the invention, the oligosaccharides comprise a mixture of (α1-2) linked mannose units and (β1-3) and/or (β1-6) glucose units (Glc(β 1-6)[Man(α1-2)[Man(α1-2)Glc(β 1-6)]Man).

In one embodiment of the animal feed additive of the invention, the oligosaccharides comprise a mixture of (β1-3) and (β1-6) glucose units Glc(β 1-3)Glc(β 1-3)Glc(β 1-6) Glc(β 1-3)Glc(β 1-3)Glc(β 1-3)Glc(β 1-3)Glc.

In one embodiment of the animal feed additive of the invention, the oligosaccharides comprise N-Acetylglucosamine as a substituent.

In one embodiment of the animal feed additive of the invention, the oligosaccharides comprise a protein residue or peptide as a substituent (for example two (β1-4) linked glucose unit linked to GlyPro).

In some embodiments of the animal feed additive of the invention, the proteins are water soluble proteins. In other embodiments of the animal feed additive of the invention, the protein hydrolysate comprises peptides, such as oligopeptides and polypeptides, and free amino acids.

In some embodiments, the peptides present in the protein hydrolysate are glycopeptides and/or peptides linked to carbohydrates. In some embodiments, the oligopeptides and/or the polypeptides in the protein hydrolysate have a molecular weight of less than 10'000 Da, preferably of 500 to 8000 Da. The peptides typically contain 2 to 20 amino acids or more. The peptides can be bioactive. The protein hydrolysate of the animal feed additive of the invention is water soluble, having improved dissolving properties and degree of hydrolysis above 2.5% In some embodiments, the protein hydrolysate of the animal feed additive of the invention comprises peptides and free amino acids, wherein the protein hydrolysate is water soluble, having improved dissolving properties and degree of hydrolysis above 2.5% and wherein peptides are oligopeptides and polypeptides, optionally linked to carbohydrates, having a molecular weight of less than 10'000 Da.

In some embodiments of the animal feed additive of the invention, lipids are selected from the group comprising fatty acids, free fatty acids, glycerolipids (such as triglycerides), glycerophospholipids, sphingolipids, sterols, prenols, saccharolipids, polyketides.

In some embodiments of the animal feed additive of the invention, the phenolic compounds are selected from the group comprising phenolic acids, flavonoids, tannins, coumarins, lignans, quinones, stilbens, and curcuminoids.

In some embodiments of the animal feed additive of the invention, the minerals are inorganic chemical compounds selected from the group comprising Al, Ca, Fe, K, Mg, Mn, Na, P, Zn, Cu, Si and/or slats thereof.

The animal feed additive of the invention is able to alter the physiological or regulatory functions in farm animals (monogastric, ruminants, fish) referring to animal performance. Thus the animal feed additive of the invention is in particular useful for feeding animals, in particular poultries such as broilers directly after birth.

The animal feed additive of the invention may be made into a premix for feed using the methods known in the art, such as disclosed in U.S. Pat. No. 5,314,692.

The animal feed additive of the invention can be used as an alternative feed additive to antibiotics and supplemented into animal diets, in particular poultries such as broilers directly after birth, for their positive effects on gut development, anti-stress, improved animal performance and overall animal health. Indeed, diets enriched with arabino-xylo-oligosaccharides (AXOS) can display prebiotic properties and improve broiler performances compared with control diet. AXOS can be fermented by health-promoting bacteria and enhance short-chain fatty acid (SCFA) and antibacterial substance production, responsible for beneficial health effects. More specifically, butyrate SCFA production increase and *Salmonella* presence reduction can be observed. Change in the intestinal microbiota also affects the growth performance of the chickens and provides increase in the feed conversion rate (FCR), feed intake and body weight. Diets comprising xylo-oligosaccharides (XOS) show also prebiotic effects. Very low incorporation rate was required to achieve improvement in animal health and performance as well as eggshell quality. The proportion of health-promoting bacteria, such as *Lactobacillus* and *Roseburia*, was higher in cecal microbiota of XOS-fed chickens, leading to an increase in acetate and butyrate SCFA production. In aquaculture, diet supplementation with AXOS or XOS also showed positive results on the intestinal microbial structure of fish, mainly siberian sturgeon and african cat-fish, as well as on their growth performance. Indeed, total SCFA production, phagocity activity, weight gain, specific growth rate and FCR can be significantly increased.

Additionally to oligosaccharides, protein hydrolysates present in the animal feed additive of the invention are effective in optimizing the nutrition of farm animals, as well as their health (particularly gut health) and well-being. Bioactive peptides are defined as the fragments of amino acids sequences in a protein that confer biological functions beyond their nutritional value. They have antimicrobial, antioxidant, antihypertensive, and immunomodulatory activities. These bioactive peptides are usually 2-20 amino acids residues in length, but some may consist of >20 amino acid residues. Additionally, protein hydrolysates may affect the sensory properties, i.e., appearance, texture, colour and flavour.

In one embodiment, the animal feed additive of the invention may be used to supplement animal diets at a desired percentage of the total diet, on a dry matter basis. The animal feed additives described herein may also be used as an animal feed or feed supplement that provides desired amounts of oligosaccharides, lipids, phenolic compounds and amino acids. The animal feed additive of the invention can be used at a high percentage of the total feed that maximizes the nutritional components of the feed for monogastric animals. The relative amount of the animal feed additive of the invention incorporated into a monograstic animal diet may depend on, for example, the species, sex, or agricultural use of the animal being fed. Additionally, the relative amount of distillers meal incorporated into a particular diet may depend on the nutritional goals of the diet.

According to an embodiment, the animal feed additive of the invention may be used in combination with other components, such as enzymes. Thus, the present invention also provides the animal feed additive further comprising enzymes selected from the group comprising xylanase, cellulase, phytase, or the combination of thereof.

The animal feed additive of the invention is suitable for oral administration. The animal feed additive of the invention may be mixed with feedstuffs and/or with drinking water.

Another aspect of the present invention provides an animal feed composition comprising an animal foodstuff and/or a basic animal diet formula and an effective amount of the animal feed additive of the invention. In a preferred embodiment, the animal feed composition is suitable for poultry. Typically the animal foodstuff and the basic animal diet are any foodstuff and diet suitable to feed animals, preferably monogastric animals, more preferably poultry. Such foodstuff and diet are well known in the art and typically contains a mixture of carbohydrates source (such as cereal grains), proteins and amino acids, fats, minerals, and vitamins.

An aspect of the present invention provides a method of feeding an animal comprising feeding a monogastric animal with the animal feed composition comprising the animal feed additive of the invention.

The animal feed composition of the invention can be used for feeding a monogastric animal, such as poultry (for example, broiler, layer, broiler breeders, turkey, duck, geese, water fowl), swine, a pet (for example dogs, cats), ruminants or fish. Preferably, the animal feed composition of the invention is used a feedstuff for monogastric animal, such as poultry (for example, broiler, layer, broiler breeders, turkey, duck, geese, water fowl).

The recommended inclusion of the animal feed additive of the invention or dose in animal feed diets depends on several factors and may vary depending: the animal kind (e.g. broiler (chicken for fattening) or piglet); animal life cycle and the feeding regime (e.g. the different feeds being used and the duration of their use; use, and commencement of use, of a creep (pre-starter) feed; age of piglets at weaning etc.). Typically, the animal feed additive of the invention is added at a dose rate between 0.001% to 15.00% or 0.001% to 5.00% (w/w complete feed), providing the improved animal performance.

The animal feed additive of the invention or the animal feed composition of the invention may be used in the form of solid or liquid preparations or alternatives thereof. Examples of solid preparations include powders, pastes, boluses, capsules, pellets, tablets, dusts, and granules which may be wettable, spray-dried or freeze-dried. Examples of liquid preparations include, but are not limited to, aqueous, organic or aqueous-organic solutions, suspensions and emulsions. In some applications, the animal feed additive of the invention may be mixed with feed or administered in the drinking water.

Another aspect of the present invention provides a method for producing the animal feed composition of the invention by mixing together an animal foodstuff and/or a basic animal diet formula and the animal feed additive of the invention.

Another aspect of the present invention provides a method of increasing weight gain in an animal, comprising feeding said animal with the animal feed additive of the invention or the animal feed composition of the invention.

An aspect of the present invention provides a method for biomass hydrolysis into animal feed additive of the invention with high digestibility and high benefits.

In an embodiment, the present invention provides a method for producing the animal feed additive according to the invention from biomass, the method comprising the steps of:

a) providing biomass;

b) optionally determining lipids, proteins and/or carbohydrates contents in the biomass;

c) optionally pre-treating the biomass;

d) optionally removing lipids and/or proteins from the biomass e) contacting the biomass with a catalyst to form a reaction mixture, wherein the catalyst is an ionic polymer or a combination of ionic polymers, the ionic polymer network, a solid-supported ionic polymers and/or a polymer membrane incorporating ionic polymers;

f) degrading the biomass in the reaction mixture to produce a liquid phase and a solid phase, wherein the liquid phase includes the animal feed additive of the invention, and the solid phase includes residual biomass;

g) isolating at least a portion of the liquid phase from the solid phase; and h) recovering the animal feed additive from the isolated liquid phase.

In one embodiment, the step e) contacting the biomass with a catalyst to form a reaction mixture consists in adding water or an appropriate organic solvent and an effective amount of the catalyst to the biomass to form a reaction mixture, wherein the catalyst is an ionic polymer of the invention or a combination of ionic polymers of the invention, the ionic polymer network of the invention, a membrane incorporating ionic polymers of the invention and/or a solid-supported ionic polymers of the invention; and degrading step f) consists in heating the reaction mixture of step e) during appropriate time and subsequently cooling to room temperature (typically 20-25° C.).

In some embodiments of the method for producing the animal feed additive of the invention from biomass, the method further comprises applying a pressure of $N_2$ or $CO_2$ during the degrading step f). The pressure may range from 20 bar to 300 bar, preferably from 20 to 150 bar.

The term "biomass," as used herein, refers to living or dead biological material that can be used in the method for producing the animal feed additive of the invention. In some embodiments, the biomass is selected from the group comprising spent yeast slurry, spent barley, pellets, nuts or (cattle) cake; a crop or crop residue: corn, soybeans, sorghum, oats, barley, copra, chaff, husks or hulls, sugar beet waste; products of decortication; fish meal; meat and bone meal; molasses; oil cake and press cake; oligosaccharides; conserved forage plants: silage; seaweed; seeds and grains, either whole or prepared by crushing, milling etc.; sprouted grains and legumes; yeast extract.

Optionally, prior to any use, carbohydrates and/or lipids contents are determined in the biomass based on the standard methods. Lipids can be determined/extracted using Folch method (Folch J, Lees M, Stanley, G H S, 1957, 226, 497-509) involving a mixture of methanol, chloroform and water (2:1:0.8, v/v/v), and phase separation afterwards. Determination of carbohydrates is performed according, for example, NREL protocol for "Determination of Structural Carbohydrates and Lignin in Biomass". For example, 1 ml of 72% sulfuric acid was added to 100 mg of biomass. The slurry was stirred for 1 h at 30° C., followed by addition of 28 ml of deionized water. Mixture was autoclaved at 120 C for 1 h, cooled to room temperature and was used for sugar analysis by HPLC and acid-soluble lignin determination using UV-spectrophotometry at 205 nm wavelength. The same hydrolysate was used for proteins analysis according to the Bradford protein assay. The residue from acid hydrolysis was washed with 100 mL of water and then dried at 105° C. to determine Klason lignin.

The optional pre-treatment of the biomass, used in the methods described herein, uses one or more methods selected from the group consisting of washing, solvent-extraction, solvent-swelling, comminution, milling, steam pre-treatment, explosive steam pre-treatment, dilute acid pre-treatment, hot water pre-treatment, alkaline pre-treatment, lime pre-treatment, wet oxidation, wet explosion, ammonia fibre explosion, organosolvent pre-treatment, biological pre-treatment, ammonia percolation, ultrasound, electroporation, microwave, supercritical $CO_2$, supercritical $H_2O$, ozone, and gamma irradiation. The optional pre-treatment of the biomass includes for example the milling of the biomass. To overcome the obstacle of the reaction rate being limited by the surface reaction and mass transfer, a pre-treatment processes of the biomass via ball milling, which leads to a reduction in crystallinity and an increase in the specific surface area of cellulosic material, is highly recommended. Depending on performed mechanical ball milling of biomass there is a decrease in structural particle size, reduction of the degree of polymerization of cellulose, and an increase in the amorphous content of cellulose.

The optional removal of lipids and/or proteins from the biomass, used in the methods described herein, provides biomass more rich in fibres product for further degradation according to step f). The lipids removal is carried out by methods known in the art, such as mechanical press, organic solvents, or supercritical $CO_2$. The protein removal is carried out by methods known in the art, such as enzymatic, alcohol, water with salts and/or surfactants, or extrusion.

Some ionic polymers used in the method of the invention for producing the animal feed additive according to the invention from biomass consists of anions and a polymeric backbone containing cations as disclosed in WO 2019/058270 A1 incorporated by reference in its entirety. Specifically, the ionic polymer (IP) used in the method of the invention for producing the animal feed additive according to the invention from biomass consists of a monomer of formula I formula I

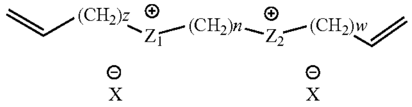

or consists of a first monomer of formula I formula I

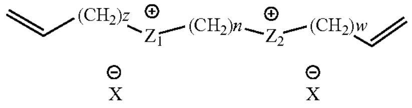

and at least one second monomer selected from the group consisting of formula II

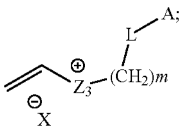

formula III

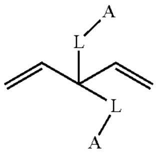

;

formula IV

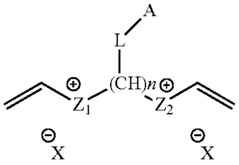

;

formula V

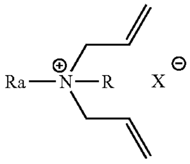

;

formula VI

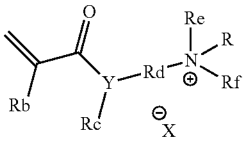

wherein n and m are independently selected from 1, 2, 3, 4, 5, 6; preferably n and m are independently selected from 1, 2, 3; most preferably n is 2 and m is 1 or 2.

z and w are independently selected from 0, 1, 2, 3; preferably z and w are independently selected from 0 and 1; most preferably z and w are 0 or 1.

$Z_1$, $Z_2$ and $Z_3$ are cations each independently selected from the group comprising:

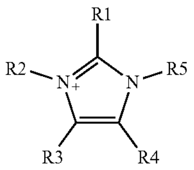
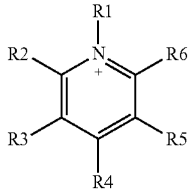
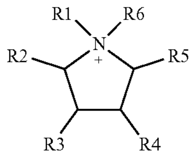
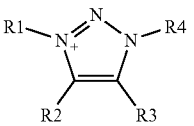
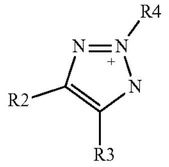
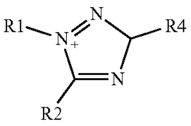
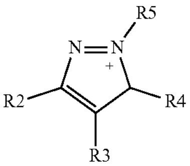
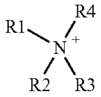
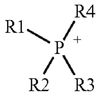
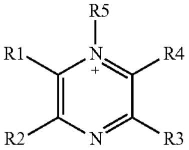
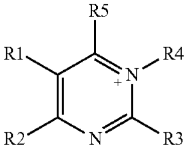
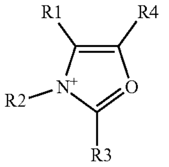
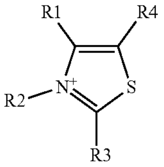
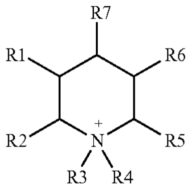
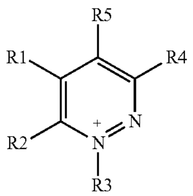
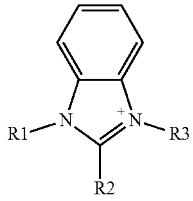
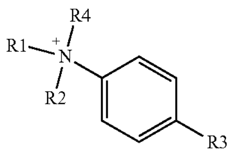

preferably $Z_1$, $Z_2$ and $Z_3$ are cations each independently selected from the group comprising:

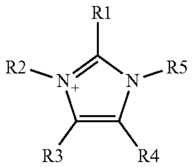
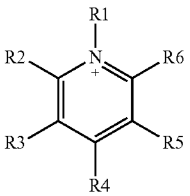
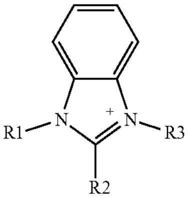
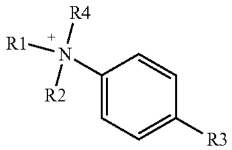

most preferably $Z_1$, $Z_2$ and $Z_3$ are cations each independently selected from the group comprising:

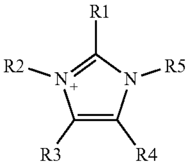
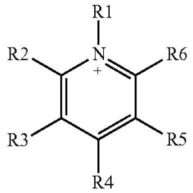

R1, R2, R3, R4, R5, R6 and R7 are each independently selected from the group comprising a bond, H, $C_1$-$C_6$ alkyl, $C_1$-$C_6$ allyl, $CH_3$—$(CH_2)$p-O—$(CH_2)$q-$CH_3$, $C_1$-$C_6$ alkoxy, $C_1$-$C_6$ alkoxyalkyl, benzyl, —$SO_3H$, —$(CH_2)$q-$SO_3H$, provided that two of R1, R2, R3, R4, R5, R6 and R7 are each a bond; preferably R1, R2, R3, R4, R5, R6 and R7 are each independently selected from the group comprising a bond, H, $C_1$-$C_6$ alkyl, provided that two of R1, R2, R3, R4, R5, R6 and R7 are each a bond; most preferably R1, R2, R3, R4, R5, R6 and R7 are each independently selected from the group comprising a bond and H, provided that two of R1, R2, R3, R4, R5, R6 and R7 are each a bond;

p and q are independently selected from 0, 1, 2, 3, 4, 5, 6;

L is an optional linker and each occurrence of L, if present, is independently selected from H, substituted or unsubstituted $C_1$-$C_{20}$ alkylene, $C_1$-$C_{20}$ alkenylene, $C_1$-$C_{20}$ alkynylene and substituted or unsubstituted $C_5$-$C_{10}$ aryl, wherein the substituents are selected from the group comprising H, —$SO_3H$, —COOH, —[P(═O)$(OH)_2$], —[P(═O)(OH)], —O—$SO_3H$, —O—COOH, —O—[P(═O)$(OH)_2$], —O—[P(═O)(OH)], preferably L is absent;

A is an optional acidic group and each occurrence of A, if present, is independently selected from the group comprising H, —$SO_3H$, —COOH, —[P(═O)$(OH)_2$], —[P(═O)(OH)], —O—$SO_3H$, —O—COOH, —O—[P(═O)$(OH)_2$], —O—[P(═O)(OH)], —$CH_2$—COOH, provided that when z and w are 0, A is present in formula IV; preferably each occurrence of A, if present, is independently selected from the group comprising H, —$SO_3H$, —COOH, —O—COOH, —$CH_2$—COOH, provided that when z and w are 0, A is present in formula IV; most preferably A is absent or occurrence of A, if present, is independently selected from the group comprising H, —COOH, —$CH_2$—COOH, provided that when z and w are 0, A is present in formula IV;

$X^-$ is selected from the group comprising $F^-$, $Cl^-$, $Br^-$, $I^-$, $ClO_4^-$, $BF_4^-$, $PF_6^-$, $AsF_6^-$, $SbF_6^-$, $NO_2^-$, $NO_3^-$, $HSO_4^-$, $SO_4^{2-}$, $PO_4^{3-}$, $HPO_4^{2-}$, $CF_3CO_2^-$, $CF_3CO_3^-$, $CO_3^{2-}$, $CF_3SO_3^-$, $C_1$-$C_6$ carboxylate, $CN^-$, $SCN^-$, $OCN^-$, $CNO^-$, $N_3^-$, tosylate, mesylate, trifluoromethanesulfonate, trifluoroethane sulfonate, di-trifluoromethanesulfonyl amino, docusate, xylenesulfonate; preferably $X^-$ is selected from the group comprising $F^-$, $Cl^-$, $HSO_4^-$, $SO_4^{2-}$, $PO_4^{3-}$, $HPO_4^{2-}$, $CF_3CO_2^-$, $CF_3CO_3^-$, $CF_3SO_3^-$; most preferably $X^-$ is selected from the group comprising $Cl^-$, $HSO_4^-$, $SO_4^{2-}$, $CF_3SO_3^-$.

Ra is $C_1$-$C_{24}$ alkyl;

Rb and Rc are each independently selected from the group comprising H and $CH_3$ or absent, preferably Rc is absent;

Rd is $C_1$-$C_{24}$ alkylene or $C_1$-$C_{24}$ alkyl, optionally substituted by $C_1$-$C_{24}$ alkyl, preferably $C_1$-$C_2$ alkylene or $C_1$-$C_2$ alkyl;

Re and Rf are each independently $C_1$-$C_{24}$ alkyl, preferably $CH_3$;

Y is N or O, provided that when Y is O, Rc is absent;

R is selected from the group comprising $C_1$-$C_{24}$ alkyl and $C_5$-$C_{10}$ aryl or is absent.

In some embodiments the ionic polymer (IP) of the present invention, the second monomer of formula VI is

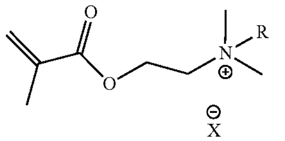

In some embodiments of the ionic polymer of the present invention, the (first) monomer of formula I is formula I

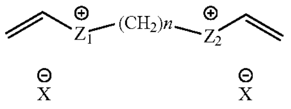

In some embodiments of the ionic polymer of the present invention, $Z_1$ and $Z_2$ are same (identical). In other embodiments, $Z_1$ and $Z_2$ are different.

In some embodiments of the ionic polymer of the present invention, when $Z_1$ and $Z_2$ is

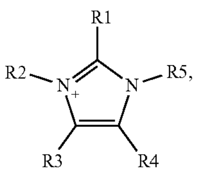

wherein R2 and R5 are bonds and R1, R3 and R4 are H, n is not 4.

In other embodiments of the ionic polymer of the present invention, when $Z_1$ and $Z_2$ is

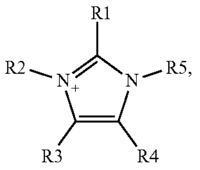

wherein R2 and R5 are bonds and n is 4, at least one of R1, R3 and R4 is not H.

In some preferred embodiments of the ionic polymer of the present invention, $C_1$-$C_6$ carboxylate are selected from the group comprising formate, acetate, propionate, butyrate, hexanoate, maleate, fumarate, oxalate, lactate, pyruvate.

The ratio between different monomers in the ionic polymers of the invention that comprises the first monomer and the second monomers can be any suitable ratio and may vary depending on the biomass to be processed. In some embodiments, the first and the second monomers are present in ratio 1:1.

According to some embodiments, the present invention provides monomers according to formula I selected from the group comprising

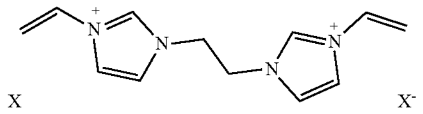

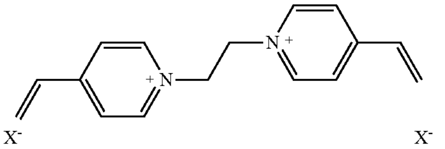

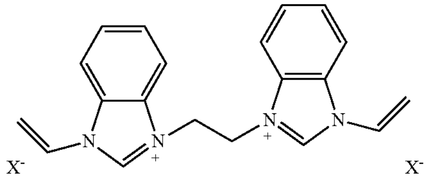

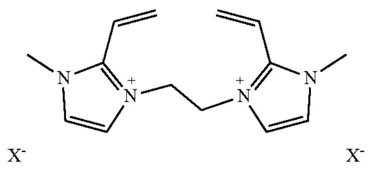

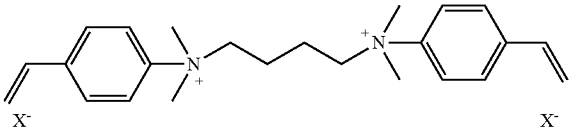

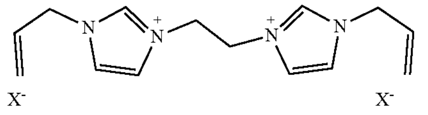

-continued

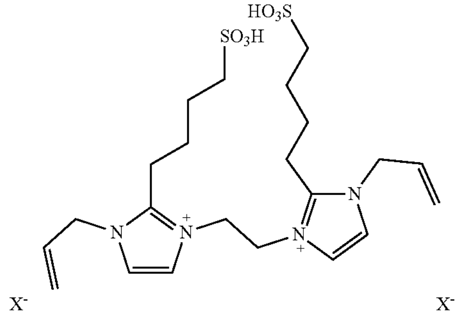

According to further embodiments, the present invention provides monomers according to formula I selected from the group comprising

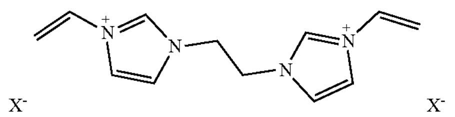

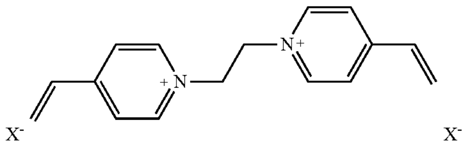

According to some embodiments, the present invention provides monomer according to

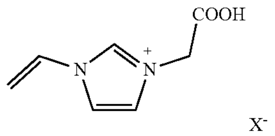

According to some embodiments, the present invention provides ionic polymers selected from the group comprising

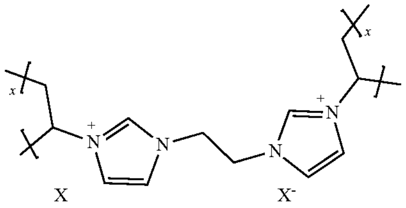

IP 1: X = $Cl^-$

IP 2: X = $CF_3SO_3^-$

-continued

IP 3

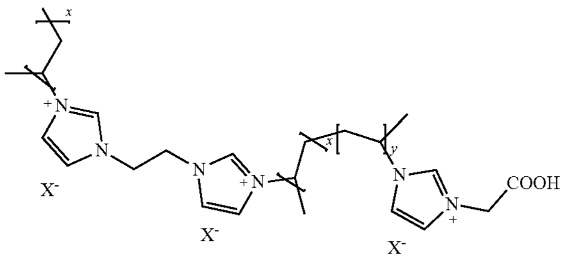

X = $Cl^-$

IP 4

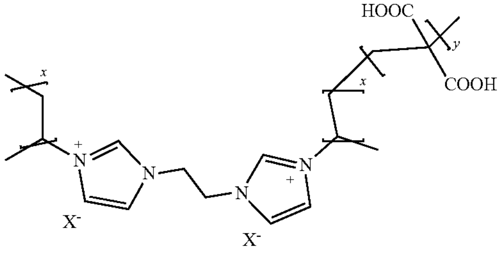

X = $Cl^-$

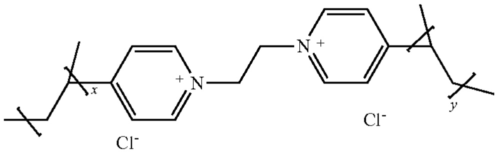

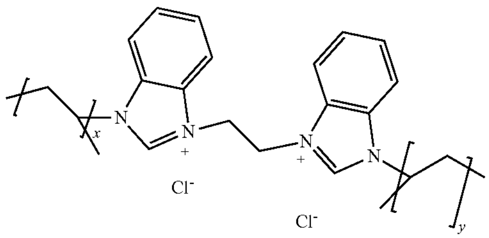

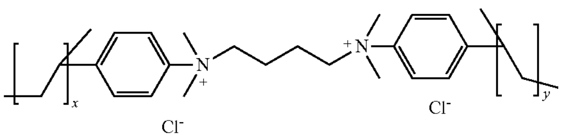

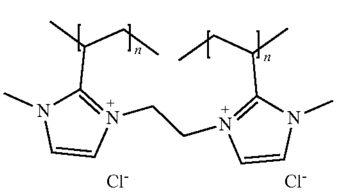

x and y are integers each independently selected within the range 1 to 1000; preferably 1 to 500 or 1 to 200; more preferably 1 to 100 or 1 to 50;

According to other embodiments, the present invention provides ionic polymers selected from the group comprising

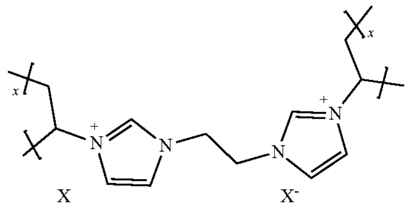

IP 1: X = $Cl^-$
IP 2: X = $CF_3SO_3^-$

IP 3

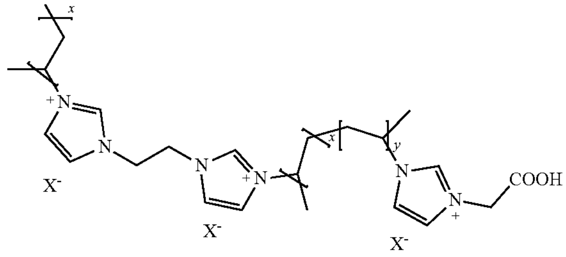

X = $Cl^-$

IP 4

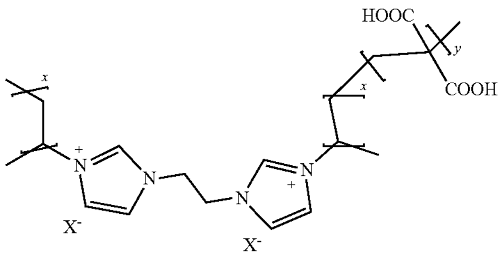

X = $Cl^-$

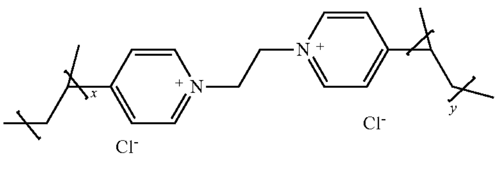

x and y are integers each independently selected within the range 1 to 1000; preferably 1 to 500 or 1 to 200; more preferably 1 to 100 or 1 to 50;

Another aspect of the present invention provides a ionic polymer (IP) consisting of a first monomer of formula I formula I

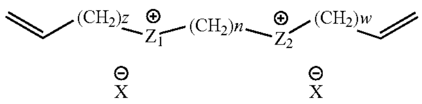

and at least one second monomer selected from the group consisting of formula II

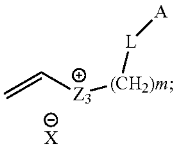

formula III

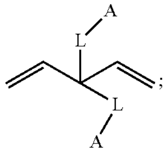

formula IV

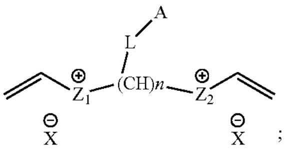

formula V

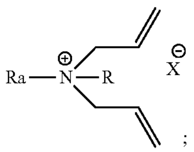

formula VI

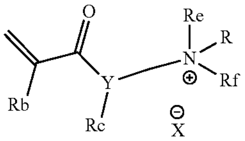

provided that at least the second monomer of formula V or at least the second monomer of formula VI is present in the ionic polymer (IP), wherein n and m are independently selected from 1, 2, 3, 4, 5, 6; preferably n and m are independently selected from 1, 2, 3; most preferably n is 2 and m is 1 or 2.

z and w are independently selected from 0, 1, 2, 3; preferably z and w are independently selected from 0 and 1; most preferably z and w are 0 or 1.

$Z_1$, $Z_2$ and $Z_3$ are cations each independently selected from the group comprising:

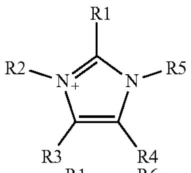

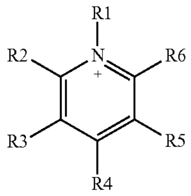

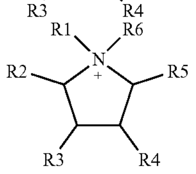

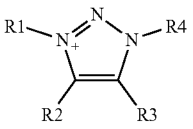

-continued

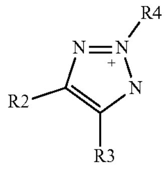
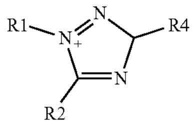
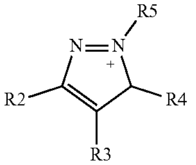
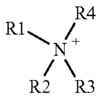
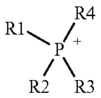
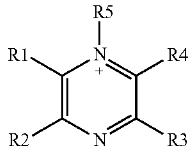
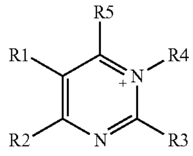
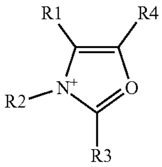
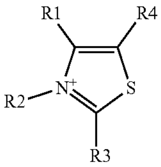
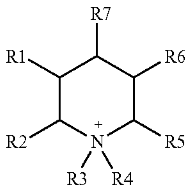
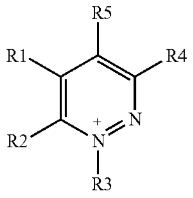
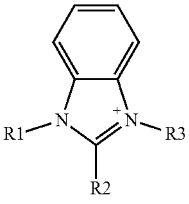
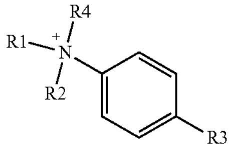

preferably $Z_1$, $Z_2$ and $Z_3$ are cations each independently selected from the group comprising:

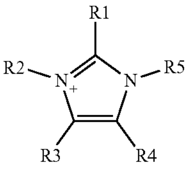
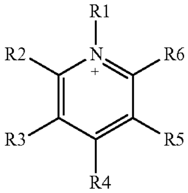
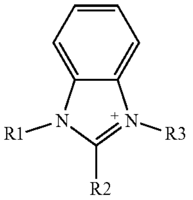
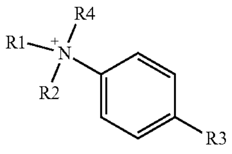

most preferably $Z_1$, $Z_2$ and $Z_3$ are cations each independently selected from the group comprising:

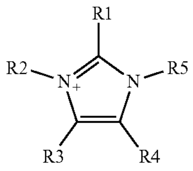
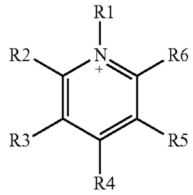

R1, R2, R3, R4, R5, R6 and R7 are each independently selected from the group comprising a bond, H, $C_1$-$C_6$ alkyl, $C_1$-$C_6$ allyl, $CH_3$—$(CH_2)$p-O—$(CH_2)$q-$CH_3$, $C_1$-$C_6$ alkoxy, $C_1$-$C_6$ alkoxyalkyl, benzyl, —$SO_3H$, —$(CH_2)$q-$SO_3H$, provided that two of R1, R2, R3, R4, R5, R6 and R7 are each a bond; preferably R1, R2, R3, R4, R5, R6 and R7 are each independently selected from the group comprising a bond, H, $C_1$-$C_6$ alkyl, provided that two of R1, R2, R3, R4, R5, R6 and R7 are each a bond; most preferably R1, R2, R3, R4, R5, R6 and R7 are each independently selected from the group comprising a bond and H, provided that two of R1, R2, R3, R4, R5, R6 and R7 are each a bond;

p and q are independently selected from 0, 1, 2, 3, 4, 5, 6;

L is an optional linker and each occurrence of L, if present, is independently selected from H, substituted or unsubstituted $C_1$-$C_{20}$ alkylene, $C_1$-$C_{20}$ alkenylene, $C_1$-$C_{20}$ alkynylene and substituted or unsubstituted $C_5$-$C_{10}$ aryl, wherein the substituents are selected from the group comprising H, —$SO_3H$, —COOH, —[P(═O)$(OH)_2$], —[P(═O)(OH)], —O—$SO_3H$, —O—COOH, —O—[P(═O)$(OH)_2$], —O—[P(═O)(OH)], preferably L is absent;

A is an optional acidic group and each occurrence of A, if present, is independently selected from the group comprising H, —$SO_3H$, —COOH, —[P(═O)$(OH)_2$], —[P(═O)(OH)], —O—$SO_3H$, —O—COOH, —O—[P(═O)$(OH)_2$], —O—[P(═O)(OH)], —$CH_2$—COOH, provided that when z and w are 0, A is present in formula IV; preferably each occurrence of A, if present, is independently selected from the group comprising H, —$SO_3H$, —COOH, —O—COOH, —$CH_2$—COOH, provided that when z and w are 0, A is present in formula IV; most preferably A is absent or occurrence of A, if present, is independently selected from the group comprising H, —COOH, —$CH_2$—COOH, provided that when z and w are 0, A is present in formula IV;

$X^-$ is selected from the group comprising $F^-$, $Cl^-$, $Br^-$, $I^-$, $ClO_4^-$, $BF_4^-$, $PF_6^-$, $AsF_6^-$, $SbF_6^-$, $NO_2^-$, $NO_3^-$, $HSO_4^-$, $SO_4^{2-}$, $PO_4^{3-}$, $HPO_4^{2-}$, $CF_3CO_2^-$, $CF_3CO_3^-$, $CO_3^{2-}$, $CF_3SO_3^-$, $C_1$-$C_6$ carboxylate, $CN^-$, $SCN^-$, $OCN^-$, $CNO^-$, $N_3^-$, tosylate, mesylate, trifluoromethanesulfonate, trifluoroethane sulfonate, di-trifluoromethanesulfonyl amino, docusate, xylenesulfonate; preferably $X^-$ is selected from the group comprising $F^-$, $Cl^-$, $HSO_4^-$, $SO_4^{2-}$, $PO_4^{3-}$, $HPO_4^{2-}$, $CF_3CO_2^-$, $CF_3CO_3^-$, $CF_3SO_3^-$; most preferably $X^-$ is selected from the group comprising $Cl^-$, $HSO_4^-$, $SO_4^{2-}$, $CF_3SO_3^-$;

Ra is $C_1$-$C_{24}$ alkyl;

Rb and Rc are each independently selected from the group comprising H and $CH_3$ or absent; preferably Rc is absent;

Rd is $C_1$-$C_{24}$ alkylene or $C_1$-$C_{24}$ alkyl, optionally substituted by $C_1$-$C_{24}$ alkyl, preferably $C_1$-$C_2$ alkylene or $C_1$-$C_2$ alkyl;

Re and Rf are each independently $C_1$-$C_{24}$ alkyl; preferably $CH_3$;

Y is N or O, provided that when Y is O, Rc is absent;

R is selected from the group comprising $C_1$-$C_{24}$ alkyl and $C_5$-$C_{10}$ aryl or is absent.

In some embodiments the ionic polymer (IP) of the invention, the second monomer of formula VI is

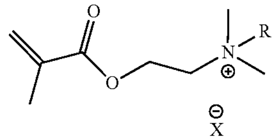

In some embodiments of the ionic polymer of the present invention, the first monomer of formula I is formula I formula I

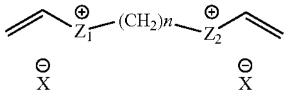

In some embodiments of the ionic polymer of the present invention, $Z_1$ and $Z_2$ are same (identical). In other embodiments, $Z_1$ and $Z_2$ are different.

In some embodiments of the ionic polymer of the present invention, when $Z_1$ and $Z_2$ is

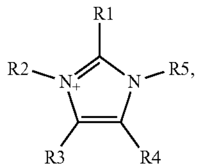

wherein R2 and R5 are bonds and R1, R3 and R4 are H, n is not 4.

In other embodiments of the ionic polymer of the present invention, when $Z_1$ and $Z_2$ is

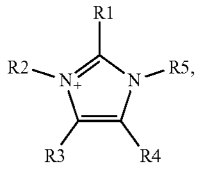

wherein R2 and R5 are bonds and n is 4, at least one of R1, R3 and R4 is not H.

Ionic polymers (IPs) of the invention can be synthesized via several methods, including but not limited to the direct polymerization of appropriate ionic species, the chemical modification of non-IPs, etc. in different solvents (water, acetonitrile, alcohols (methanol, ethanol, propanol etc.), toluene, TIF) (see Examples). Polymerization may include different approaches, e.g. free radical polymerization, living/controlling radical polymerization, reversible addition-fragmentation transfer, ionic and coordination polymerization. The anionic structure can be designed according to preference before or after polymerization. The resulting ionic polymer (IP) combines the general properties of the ionic monomer and the enabling properties of a solid catalyst due to the presence of acidic groups. In an embodiment of the invention, a salt is prepared with a cation and an anion, wherein one of or at least one of the cation and the anion contain vinyl groups that can be polymerized using AIBN or other initiator. It is essentially a very simple method and the ionic polymer is purified by removal of the excess AIBN by washing and filtration. In a specific embodiment of the invention, a salt that is composed of the 1-(1-vinylimidazolium)ethyl-3-vinylimdazolium] [dichloride]) is prepared. This salt, a pure compound, is then polymerized using the radical initiator AIBN. The ionic polymer is purified by removal of the excess AIBN by washing and filtration. As alternative to dichoride anion, a ditriflate anion can be obtained via anion exchange reaction prior polymerization.

The present invention also provides an ionic polymer network comprising cross-linked one or more ionic polymers of the invention.

In some embodiments, the ionic polymer network of the invention further comprises itaconic acid, citric acid and/or 1,4 butanediol.

In other embodiments, the ionic polymer network of the invention further comprises one or more metal catalysts. In some embodiments, the metal catalyst is a metal salt. In preferred embodiments anion in metal salt is selected from the group comprising $F^-$, $Cl^-$, $Br^-$, $I^-$, $ClO_4^-$, $BF_4^-$, $PF_6^-$, $AsF_6^-$, $SbF_6^-$, $NO_2^-$, $NO_3^-$, $HSO_4^-$, $SO_4^{2-}$, $PO_4^{3-}$, $HPO_4^{2-}$, $CF_3CO_2^-$, $CF_3CO_3^-$, $CO_3^{2-}$, $CF_3SO_3^-$, $C_1$-$C_6$ carboxylate, $CN^-$, $SCN^-$, $OCN^-$, $CNO^-$, $N_3^-$, tosylate, mesylate, trifluoromethanesulfonate, trifluoroethane sulfonate, di-trifluoromethanesulfonyl amino, docusate, xylenesulfonate salts, and metal ion is selected from the group comprising Na, Ba, Sr, Ca, Cd, Sn, Pb, Fe, Cu, Zn, Zr, Mn, Co, Ni, Li, Al, Cr, Mg, Mo, Hg, Ag, Au, Pt, Rh, Re, Ti, Pb, Bi, Ga, In, Sn, Ir, La, Hf, Ta, W, Os.

In some preferred embodiments, $C_1$-$C_6$ carboxylate are selected from the group comprising formate, acetate, propionate, butyrate, hexanoate, maleate, fumarate, oxalate, lactate, pyruvate.

The ionic polymer network of the invention comprising one or more metal catalysts provides better stability and reusability of the ionic polymer-metal combinations.

The preparation of the ionic polymer network of the invention with one or more metal catalysts typically consists in mixing or refluxing the ionic polymer network and metal salt in water/organic solvent overnight. See for example J. Am. Chem. Soc., 2012, 134, 11852-11855; Chem. Cat. Chem., 2016, 8, 2508-2515; J. Org. Chem., 2011, 76 (24), pp 10140-10147; Inorg. Chem., 2006, 45, 6396-6403.

The ionic polymers of the invention can be incorporated in membranes or attached to solid supports.

Another aspect of the invention provides membranes composed of ionic polymers of the invention. In some embodiments, the invention provides a polymer membrane comprising one or more ionic polymers of the invention. By adding appropriate copolymer (for example acrylic acid) to the salt used for preparation of ionic polymers of the invention and then polymerize the mixture it is possible to generate a polymer membrane. An approach for membrane formation is based on the template-free method via simple ionic complexations when an ionic monomer is copolymerized with appropriate organic acid/acid derivative (see Tauber K. et al, *Polym. Chem.*, 2015, 6, 4855-4858; Tauber K.

et al, *ACS Macro Lett.,* 2015, 4(1), 39-42; Zhang S. et al, *Chem. Sci.,* 2015, 6, 3684-3691). As example, ionic monomer was dissolved in DMSO and stirred for 2 h at 60° C. The transparent solution was then poured onto a glass plate and the solvent was evaporated at 80° C. in an oven. The resulting non-porous dry polymer film was subsequently immersed into aqueous ammonia (0.2 wt %) overnight for pore formation and electrostatic complexation. The membrane was detached easily from the glass plate and washed several times with water.

Another aspect of the invention provides solid-supported ionic polymers. In some embodiments, the invention provides a solid support having at least one surface comprising one or more ionic polymers of the invention. Supported ionic polymers can be immobilized on different materials as a support: silicon or carbon (nanotube, wire) source, graphene or graphene oxide, zeolites, metal/metals alloys or metal/metal alloy oxides. As example, $FeO_x$ support has been oxidized in the oven in presence of oxygen at high temperature (500° C.) and its surface was modified with mixture of silanes dissolved in ethanol in presence of HCl afterwards. After drying at room temperature, the support was uniformly impregnated with methanol solution of ionic polymer and AIBN. After drying at room temperature, the obtained material was placed in the oven at 95° C. for 2 h. By repeating the impregnation process the desire polymer loading might be achieved. Another example is stainless steel membrane comprising ionic polymers of the invention. A mixture containing ionic monomer (0.2-0.5, molar ratio), acrylic acid (0.1-0.6, molar ratio), and benzoin ethylether (1 wt %, as a photo-initiator) were dissolved in methanol to achieve a homogeneous solution, which was then dispersed by wettening onto stainless steel membrane and photo-crosslinked at room temperature by irradiation with UV light of 250 nm wavelength.

Ionic polymer attachment is also possible through surface grafting, which requires activation of the support by UV or $O_3$, $O_2$, $H_2$ or air plasmas. It involves the creation of reactive sites (radicals) on the polymer surface followed by the covalent linkage of a preformed polymer or, more commonly, by the polymerization of a monomer from those radical sites (see Alves P. et al, Colloids and Surfaces B: Biointerfaces, Volume 82, Issue 2, 1 Feb. 2011, 371-377; Barbey R. et al., *Chem. Rev.,* 2009, 109(11), 5437-5527). Another copolymer or polymerization initiator might also be used during the polymerisation process (as in case of membrane formation).

In some embodiments of the method for producing the animal feed additive of the invention, the organic solvent is selected from the group comprising alcohol (such as methanol, ethanol, butanol, ethylene glycol, etc.), ether (such as dimethoxyethane, diglyme, butyl methyl ether, etc.), ketone (such as methyl isobutyl ketone, N-methyl-2-pyrrolidone, etc.), eutectic solvent (such as glycerol, choline chloride, octanoic acid, tetrabutylammonium chloride, poly (ethylene glycol), choline chloride, lactic acid, glycine).

In some embodiments of the methods of the present invention, recovering the animal feed additive can be done by any technic known in the art, such as filtration, centrifugation or gravity settling. After the recovering, the animal feed additive can be used it is, in a liquid form, or concentrated or dried to a powder form.

The effective amount of the ionic polymers of the invention or a combination thereof used in the methods described herein can depend on several factors including, for example, the type of the biomass, the amount of the biomass, the content of proteins, carbohydrates and/or lipids in the biomass, the type and number of pre-treatment(s) applied to the biomass, and the reaction conditions (such as temperature and time). An effective amount of the ionic polymer of the invention refers to an amount sufficient to degrade biomass into the animal feed additive of the invention. In some embodiments, the effective amount of the ionic polymer of the invention is usually 0.05:1 w/w to 10:1 w/w, 0.5:1 w/w to 10:1 w/w, 1:1 w/w to 1:5 w/w, preferably 0.1:1 w/w to 1:5 w/w compared to in the biomass loading.

The ratio biomass to water used in the methods described herein can depend on several factors, including for example the type of biomass and the amount of biomass. In some embodiments, the ratio biomass to water or organic solvent (such as alcohol, ether, ketone, eutectic solvent) used in the methods described herein is ranging from 1:100 w/v to 1:1 w/v, preferably 1:50 w/v to 1:10 w/v.

The preferred temperature profile for the heating used in the methods described herein depends on the biomass starting material being used and also the intended monomer and oligomer mixture being produced. The heating temperature should preferably be held at a maximum of 170° C., in some embodiments at a maximum of 150° C. In some embodiments, the heating temperature is between 50° C. and 170° C., or between 80° C. and 170° C. preferably between 100° C. to 150° C. or between 100° C. to 130° C. Preferably, for small-scale applications, the heating is done in a high-pressure autoclave reactor, which after sealing, is heated for appropriate reaction time and temperature.

In some embodiments, the appropriate reaction time in the methods described herein is for example between 10 minutes and 10 hours, preferably between 0.5 hour and 5 hours, or 0.5 hours and 3 hours, or between 1 hour and 3 hours, depending on the type and amount of biomass.

The method for producing the animal feed additive of the invention operates at moderate temperatures, typically less than 150° C., whereas the prior art methods needs temperatures of more than 150° C. In addition, the method for producing the animal feed additive of the invention provides fewer by-products, which allows easier recovery of the desired products.

Another aspect of the present invention provides an animal feed additive obtained by the method of the invention for producing the animal feed additive.

In an embodiment of the invention, the animal feed additive obtained by the method of the invention for producing the animal feed additive, comprises oligosaccharides, proteins and/or protein hydrolysates, lipids, phenolic compounds and minerals, wherein the oligosaccharides are selected from the group comprising glucans, xylans, arabinans and/or mannans, and wherein degree of polymerisation (DP) of the oligosaccharides is DP1 to DP30. In another embodiment, the animal feed additive obtained by the method of the invention for producing the animal feed additive, consists of oligosaccharides, proteins, lipids, phenolic compounds, minerals and moisture, wherein the oligosaccharides are selected from the group comprising glucans, xylans, arabinans and/or mannans, and wherein degree of polymerisation (DP) of the oligosaccharides is DP1 to DP30. In a further embodiment, the animal feed additive obtained by the method of the invention for producing the animal feed additive, comprises (in wt %)

Total oligosaccharides: 25% to 100%, preferably 25% to 95% or 25% to 75%

Proteins and/or protein hydrolysates: 0% to 55%, preferably 5% to 55% or 10% to 55%

Lipids: 0% to 5%, preferably 0.5% to 2%

Phenolic compounds: 0% to 55%, preferably 2.5% to 55%

Minerals: <10%, preferably 0% to 4%, preferably 2.5% to 4%

Moisture: <10%, preferably <5% or 0% to 5% wherein the oligosaccharides are selected from the group comprising

Glucans: 0% to 40%, preferably 3% to 40%, by weight of total oligosaccharides

Xylans: 0% to 50%, preferably 10% to 50%, by weight of total oligosaccharides

Arabinans: 0% to 50%, preferably 0% to 40%, preferably 3% to 40%, by weight of total oligosaccharides Mannans: 0% to 30%, preferably 2% to 30%, by weight of total oligosaccharides and wherein distribution of degree of polymerisation (DP) of said oligosaccharides is DP1: 0% to 30%, preferably 1% to 30%

DP2 to DP30: >70%, preferably 70% to 75% or 70% to 100%.

According to another embodiment, the animal feed additive obtained by the method of the invention for producing the animal feed additive, consists of (in wt %)

Total oligosaccharides: 25% to 100%, preferably 25% to 95% or 25% to 75%

Proteins and/or protein hydrolysates: 0% to 55%, preferably 5% to 55% or 10% to 55%

Lipids: 0% to 5%, preferably 0.5% to 2%

Phenolic compounds: 0% to 55%, preferably 2.5% to 55%

Minerals: <10%, preferably 0% to 4%, preferably 2.5% to 4%

Moisture: <10%, preferably <5% or 0% to 5% wherein the oligosaccharides are selected from the group comprising

Glucans: 0% to 40%, preferably 3% to 40%, by weight of total oligosaccharides

Xylans: 0% to 50%, preferably 10% to 50%, by weight of total oligosaccharides

Arabinans: 0% to 50%, preferably 0% to 40%, preferably 3% to 40%, by weight of total oligosaccharides Mannans: 0% to 30%, preferably 2% to 30%, by weight of total oligosaccharides and wherein distribution of degree of polymerisation (DP) of said oligosaccharides is DP1: 0% to 30%, preferably 1% to 30%

DP2 to DP30: >70%, preferably 70% to 75% or 70% to 100%.

An important advantage of the ionic polymers of the invention or a combination thereof, membranes incorporating ionic polymers of the invention and/or solid-supported ionic polymers of the invention and use thereof for biomass hydrolysis, decomposition or degradation is their use in one-pot systems for decomposition and selective extracting the aforementioned animal feed additive from the biomass. Further, ionic polymers of the invention are insoluble, thus does not mix with the animal feed additive of the present invention.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended claims, and all changes which come within the meaning and range of equivalency are intended to be embraced therein.

The foregoing description will be more fully understood with reference to the following Examples. Such Examples, are, however, exemplary of methods of practising the present invention and are not intended to limit the application and the scope of the invention.

EXAMPLES

Preparation of Monomer of Formula VI

To prepare cationic DMAEMAQ 30 mmol of DMAEMA were dissolved in an appropriate amount of solvent (solvent may be THF, acetonitrile, DCM, chloroform, diethyl ether, etc.) followed by careful addition of 36 mmol of RX, where X may be halide, HSO4- or R'SO4- and R is alkyl or aryl. The reaction mixture was stirred at room temperature for 12 h. Afterwards, the precipitate was filtered and washed with addition of cold hexane. Finally, the obtained product was dried for 8 h under vacuum to yield the crystalline solid of corresponding DMAEMAQ monomer.

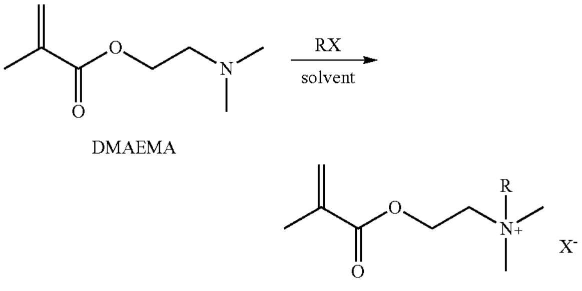

DMAEMA

DMAEMAQ

Preparation of the Animal Feed Additive (Yeast Hydrolysate) from Yeast Slurry 122 g of yeast slurry (dry bases) suspended in 1.7 L of water together with ionic polymer catalyst "IP1" were stirred at 140° C. for 1.5 h. After reaction, the mixture was cooled to room temperature, filtered and the liquid phase was dried using spray drier. The obtained product (the animal feed additive) was analysed and used for poultry trials. The obtained animal feed additive (yeast slurry hydrolysate) contained 29.6% of oligosaccharides, with 19.2% and 10.4% as glucan and mannan respectively, with the DP<20.

Preparation of the Animal Yeast Additive (Yeast Hydrolysate) from Dry Yeast Cell 300 g g of dry yeast was mixed with 1.5 g of ionic polymer catalyst "IP3" and 4 L of $H_2O$ for 1 h at 160° C. After reaction, the mixture was cooled to room temperature, filtered, concentrated and the animal feed additive was recovered from liquid phase using alcohol precipitation. The obtained dry animal feed additive (yeast hydrolysate) contained 31% of oligosaccharides, with 19% and 12% as glucan and mannan respectively, with the DP<20.

Preparation of the Animal Feed Additive EMB1 from Brewers' Spent Grains (BSG)

500 g of brewers' spent grains (BSG) (dry bases) suspended in 3.75 L of water together with ionic polymer catalyst "IP1" were stirred at 140° C. for 1 h. After reaction, the mixture was cooled to room temperature, filtered and the liquid phase was dried using spray drier. The obtained dried powdered product (the animal feed additive) EMB1 was analysed and used for poultry trials. EMB1 contained 59% of oligosaccharides, with 41% and 18% as arabinoxylan and glucan respectively. The composition of EMB1 is presented below:

| Components | g/100 g product |
|---|---|
| Oligosaccharides total | 55-75 |
| Glucan | 10-25 |
| Xylan | 26-35 |
| Arabinan | 13-20 |
| Protein/protein hydrolysates | 20-30 |
| Lipids | 1-5 |
| Phenolic compounds | 2.5-5 |
| Minerals | <7 |
| Moisture | <8 |

Preparation of the Animal Feed Additive EMB2 from Brewers' Spent Grains 267 g of BSG (dry bases) suspended in 4 L of water were stirred at 90° C. for 1 h. Afterwards, the mixture was cooled to room temperature, filtered and solid phase was resuspended in 2.850 L of water together with "IP1" and stirred at 140° C. for 1 h. After reaction, the mixture was cooled to room temperature, filtered and the liquid phase was dried using spray drier. The obtained dried powdered product (the animal feed additive) EMB2 was analysed and used for poultry trials. EMB2 contained 62% of oligosaccharides, with 52% and 10% as arabinoxylan and glucan respectively. The composition of EMB1 is presented below:

| Component | g/100 g product |
|---|---|
| Oligosaccharides total | 59-75 |
| Glucan | 2-9 |
| Xylan | 28-40 |
| Arabinan | 14-21 |
| Protein/protein hydrolysates | 15-25 |
| Lipids | 1-3 |
| Phenolic compounds | 1-3 |
| Minerals | <8 |
| Moisture | <8 |

Preparation of the Animal Feed Additive EMB3 from Buckwheat Hull 400 g of buckwheat hull (dry bases) suspended in 4 L of water together with ionic polymer catalyst "IP1" were stirred at 140° C. for 2 h. After reaction, the mixture was cooled to room temperature, filtered and the liquid phase was dried using spray drier. The obtained dried powdered product (the animal feed additive) EMB3 was analysed and used for poultry trials. EMB3 contained 66% of oligosaccharides, with 33% and 33% as xylan and glucan respectively. The composition of EMB3 is presented below:

| Component | g/100 g product |
|---|---|
| Carbohydrates total | 50-70 |
| Glucan | 22-35 |
| Xylan | 25-35 |
| Arabinan | 0-5 |
| Protein/protein hydrolysates | 2-7 |
| Lipids | 2-8 |
| Phenolic compounds | 5-15 |
| Minerals | <10 |
| Moisture | <8 |

Responses of Broiler Chickens Fed with Addition of the Animal Feed Additive (Yeast Hydrolysate) to their Diet The use of animals and experimental protocol was approved by the Institutional Animal Experiment Committee. A diet was formulated to be balanced for energy and nutrients for young broiler chicks (0-28 days of life) (Table 1 and 2).

TABLE 1

| Diet composition | |
|---|---|
| Ingredient Name | Kgs |
| CORN, YELLOW, GRAIN | 560.38 |
| SOYBEAN MEAL DEHULLED, SOLVENT | 393.11 |
| FAT, VEGETABLE | 16.31 |
| CALCIUM CARBONATE | 10.48 |
| DICALCIUM PHOSPHATE | 9.74 |
| Methionine MHA | 3.24 |
| SALT, PLAIN (NaCl) | 2.88 |
| L-LYSINE | 1.82 |
| Trace Mineral | 0.75 |
| Vitamin premix | 0.65 |
| L-Threonine 98.5 | 0.52 |
| quantum blu | 0.11 |

TABLE 2

| Nutrient Analysis | |
|---|---|
| Nutrient Name | Amount |
| DRY MATTER | 85.66 |
| PROTEIN, CRUDE | 22 |
| FAT, CRUDE | 3.9 |
| FIBER, CRUDE | 2.22 |
| CALCIUM | 0.9 |
| PHOS. TOTAL | 0.57 |
| PHOS., AVAILABLE | 0.45 |
| M.E. POULTRY | 3,008.00 |
| METHIONINE | 0.59 |
| LYSINE | 1.28 |
| TRYPTOPHAN | 0.29 |
| THREONINE | 0.85 |
| SODIUM | 0.18 |
| POTASSIUM | 0.91 |
| CHLORIDE | 0.2 |
| dig methionine | 0.56 |
| dig cysteine | 0.29 |
| dig lysine | 1.18 |
| dig tryptophan | 0.28 |
| dig threonine | 0.78 |
| dig isoleucine | 0.86 |
| dig histidine | 0.5 |
| dig valine | 0.9 |
| dig leucine | 1.69 |
| dig arginine | 1.27 |
| dig phenylalanine | 1 |
| digTSAA | 0.88 |

Male broiler (Rearing Cobb) chicks were obtained as day-olds from a commercial hatchery. The chicks were individually weighed and allocated to 6 cages (8 chicks per cage) so that the average bird weight per cage was similar. The 8 dietary treatments (Table 3) were then randomly assigned to 6 cages each. The birds were challenged with coccidal infection (by *E. maxima* (~5,000 oocysts)) on $14^{th}$ day of their life and with clostridial infection (*C. perfringens* (~108 cfu/ml)) on $19\text{-}21^{st}$ day of their life. The animal feed additive of the invention (yeast slurry hydrolysate and dry yeast hydrolysate in a powder form) were introduced in a premix to demonstrate their beneficial effect and were added to the mixer during diet preparation. Body weights were recorded at Day 0, 14, 21, 28. Feed intake was recorded at Day 21 and 28. Mortality was recorded daily. Lesion scoring was done on Day 28. The data were analysed using the GLM procedure of SAS.

TABLE 3

Experimental treatments

| | Challenge | | Concentration in feed (ppm) | | |
|---|---|---|---|---|---|
| | Coccidium | Clostridium | Stafac | DY-H | YS-H |
| 1. Non-medicated | + | + | | | |
| 2. Non-medicated | + | − | | | |
| 3. Stafac (antibiotic control) | + | + | 20 | | |
| 4. DY-H 0.1% | + | + | | 1000 | |
| 5. YS-H 0.1% | + | + | | | 1000 |
| 6. YS-H 0.05% | + | + | | | 500 |
| 7. YS-H 0.025% | + | + | | | 250 |
| 8. YS-H 0.01% | + | + | | | 100 |

YS-H is the yeast slurry hydrolysate; DY-H is the dry yeast hydrolysate

The obtained results (FIG. 1) show that chickens fed with DY-H significantly improved body weight gain (BWG) during Day 14-28, while addition of YS-H not significantly but tended to improve BWG at every dose during Day 14-28. Both DY-H and YS-H at lower doses (excl. 0.01%) significantly improved FCR during Day 14-28. The efficacy of YS-H tended to slightly decrease in a dose-dependent manner.

Figure 2:
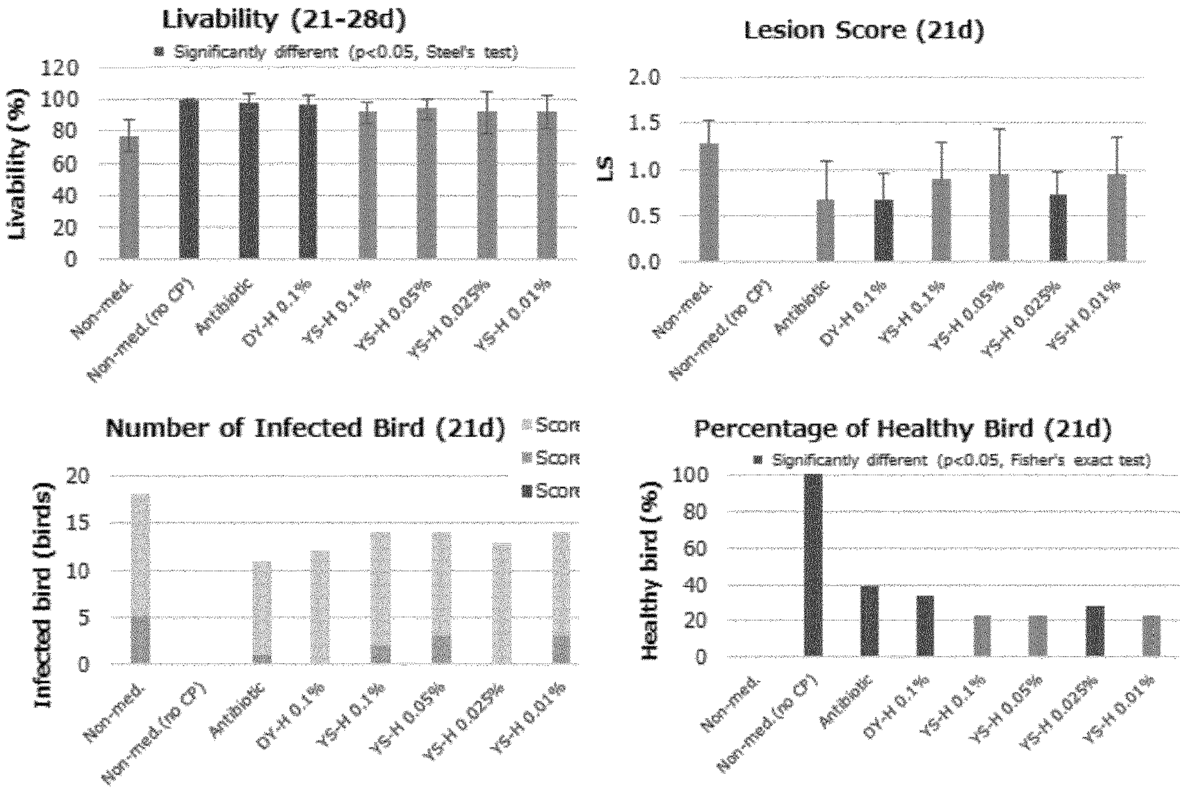
FIG. 2 shows assessment of the mortality rate and healthy birds status.

Furthermore, addition of DY-H significantly reduced mortality during Day 21-28 (FIG. 2). YS-H not significantly but tended to reduce mortality at every dose during Day 21-28. Both DY-H and YS-H at lower doses alleviated intestinal lesion. DY-H tended to be more effective compared to YS-H.

Responses of Broiler Chickens Fed with Addition of the Animal Feed Additives

Healthy male broiler (Cobb 430 Y) chicks were obtained as day-olds from a commercial hatchery. The chicks were individually weighed and allocated to 96 cages (25 chicks per cage) in an open sided house. The 8 dietary treatments (Table 1) and control were then randomly assigned to 12 cages each and a mush type of diet was applied. Salinomycine was used as a coccidiostat for all the chicks and no other growth promoter or mycotoxin binder were used. Body weights were recorded at Day 1, 21, 42. Pen feed intake was recorded at Day 1, 21 and 42. Mortality and health status were recorded daily. Temperatures peaked at 37 during the first week and remained high (above 33° C.) for most days of the trial, hence birds were likely heat stressed and this would affect the performance. No humidity control existed in the house.

TABLE 4

Experimental treatments used for poultry study

| Treatment | Product | Inclusion level per tonne |
|---|---|---|
| 1. Control | None | |
| 2. X-EMB1 | xylanase enzyme - EMB1 | 100 g - inclusion 1 |
| 3. X-EMB1 | xylanase enzyme - EMB1 | 100 g - inclusion 2 |
| 4. X-EMB1 | xylanase enzyme - EMB1 | 100 g - inclusion 3 |
| 5. X-EMB2 | xylanase enzyme - EMB2 | 100 g - inclusion 4 |

TABLE 4-continued

Experimental treatments used for poultry study

| Treatment | Product | Inclusion level per tonne |
|---|---|---|
| 6. X-EMB2 | xylanase enzyme - EMB2 | 100 g - inclusion 5 |
| 7. X-EMB2 | xylanase enzyme - EMB2 | 100 g - inclusion 6 |
| 8. X-EMB3 | xylanase enzyme - EMB3 | 100 g - inclusion 7 |
| 9. X-EMB3 | xylanase enzyme - EMB3 | 100 g - inclusion 8 |

TABLE 5

Diet formulation and treatment identification

| Ingredient | Starter 0-18 d | Finisher 18-42 d |
|---|---|---|
| Corn | 41.25% | 46.69% |
| Wheat-Feed | 25.00% | 25.00% |
| Soybean meal 48 | 29.26% | 24.39% |
| Soy oil | 1.00% | 1.59% |
| Salt | 0.34% | 0.32% |
| DL Methionine | 0.30% | 0.15% |
| Lysine HCl | 0.26% | 0.12% |
| Threonine | 0.06% | 0.00% |
| Limestone | 1.01% | 0.85% |
| Mono Dical Phos | 1.01% | 0.38% |
| Quantum Blue | 0.01% | 0.01% |
| Vitamin premix | 0.50% | 0.50% |
| Crude protein % | 20.19 | 18.00 |
| Poult ME kcal/kg | 3,000.0 | 3,100.0 |
| Pig DE Kcal | 3,448.0 | 3,488.4 |
| Calcium % | 0.98 | 0.78 |
| Phos % | 0.75 | 0.60 |
| Avail Phos % | 0.48 | 0.35 |
| Fat % | 3.35 | 4.14 |
| Fibre % | 2.60 | 2.56 |
| Met % | 0.60 | 0.43 |
| Cys % | 0.35 | 0.32 |
| Me + Cys % | 0.95 | 0.75 |
| Lys % | 1.25 | 1.00 |
| His % | 0.54 | 0.49 |
| Tryp % | 0.24 | 0.21 |
| Thr % | 0.81 | 0.67 |
| Arg % | 1.31 | 1.16 |
| Iso % | 0.83 | 0.74 |
| Leu % | 1.63 | 1.50 |
| Phe % | 0.98 | 0.89 |
| Tyr % | 0.72 | 0.65 |
| Val % | 0.92 | 0.83 |
| Gly % | 0.83 | 0.75 |
| Ser % | 0.96 | 0.87 |
| Phe + Tyr % | 1.70 | 1.54 |
| Phytate P % | 0.22 | 0.21 |
| Na % | 0.19 | 0.18 |
| Cl % | 0.30 | 0.26 |
| K % | 0.86 | 0.77 |
| Linoleic acid % | 1.46 | 1.78 |
| Na + K—Cl | 217.34 | 202.11 |
| DUA | 409.49 | 387.92 |
| Sulphur % | 0.20 | 0.18 |
| Magnesium | 0.17 | 0.16 |
| Betaine | 0.32 | 0.32 |
| Choline | 1,254.74 | 1,155.66 |
| Poult ME MJ/kg | 12.55 | 12.97 |
| Poult NE Kcal/kg | 1,957 | 2,052 |
| Gly + ser | 1.79 | 1.62 |

Comments

Mortality was low throughout the trial and not influenced by treatment.

TABLE 6

| Mortality data for each week of the study % of Cumulative Mortality | | | | | | |
|---|---|---|---|---|---|---|
| Treatment | 1 wk | 2 wk | 3 wk | 4 wk | 5 wk | 6 wk |
| 1. Control | 0.000 | 0.615 | 0.615 | 1.231 | 1.231 | 1.846 |
| 2. X-EMB1 (inclusion 1) | 0.000 | 0.308 | 1.231 | 1.538 | 1.538 | 1.538 |
| 3. X-EMB1 (inclusion 2) | 0.000 | 0.615 | 1.846 | 2.154 | 2.769 | 2.769 |
| 4. X-EMB1 (inclusion 3) | 0.000 | 0.000 | 0.000 | 0.000 | 0.000 | 0.000 |
| 5. X-EMB2 (inclusion 4) | 0.000 | 0.000 | 0.615 | 0.923 | 1.846 | 3.385 |
| 6. X-EMB2 (inclusion 5) | 0.000 | 0.000 | 0.615 | 1.231 | 1.538 | 1.846 |
| 7. X-EMB2 (inclusion 6) | 0.000 | 0.308 | 0.615 | 0.923 | 0.923 | 0.923 |
| 8. X-EMB3 (inclusion 7) | 0.000 | 0.615 | 0.615 | 0.923 | 1.231 | 1.846 |
| 9. X-EMB3 (inclusion 8) | 0.000 | 0.923 | 1.538 | 1.538 | 1.538 | 2.154 |

Overall performance was good to Day 21 of age given the fact that the birds were heat stressed fed a low nutrient density mash-based diet, and thus room for improvement was limited. Performance to Day 42 was average, however, given the diet and heat stress, the results are very positive.

Figure 3:
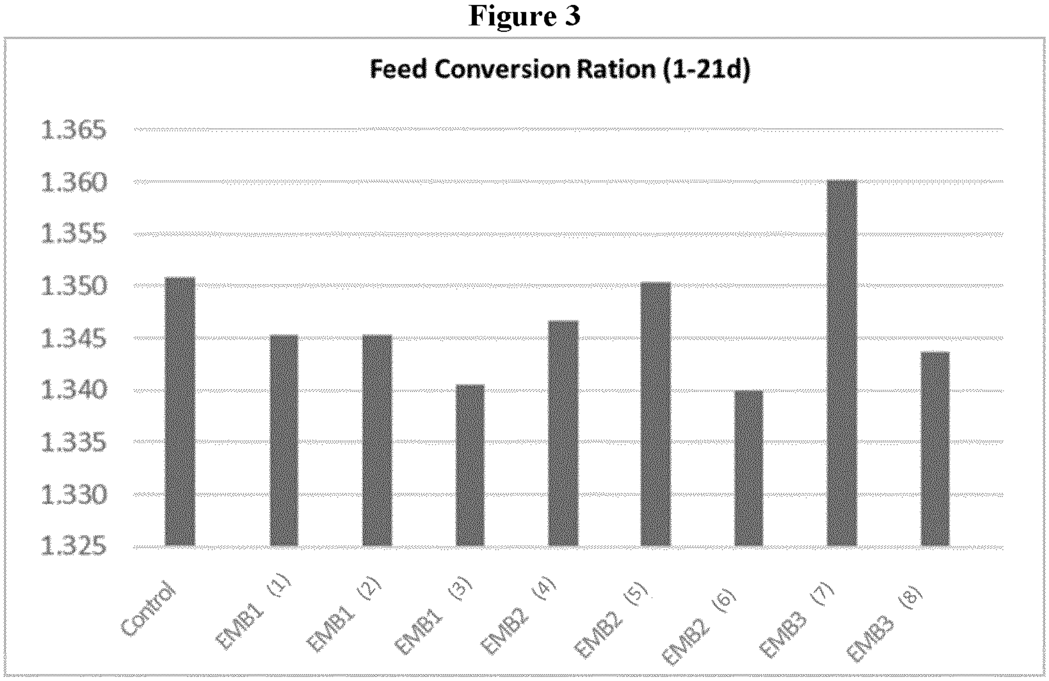
FIG. 3 shows FCR for Day 1-21.

FCR during Day 1-21 (FIG. 3) was significantly improved showing the excellent control of variation at this site.

Carcass data (Table 7) did show significant responses but not in key RTC or breast meat yields. Liver weight was reduced with most treatments which may be reflective of all treatments tending to reduce loading on the animals inflammatory and nutrient repackaging systems which is thought to be beneficial. Abdominal fat was greatest in the EMB1 (inclusion 2) followed by the EMB3 (inclusion 8) treatment. Abdominal fat is often used as a gauge of energy sufficiency and in this regard these treatments seemed to have a benefit.

TABLE 7

| Carcass data | | | | | |
|---|---|---|---|---|---|
| Treatment | RTC | Breast | Ab Fat | Liver | Gizzard |
| 1. Control | 784.2 | 271.2 | 11.1 | 16.3 | 13.9 |
| 2. X-EMB1 (inclusion 1) | 776.1 | 271.9 | 10.5 | 14.9 | 13.8 |
| 3. X-EMB1 (inclusion 2) | 775.3 | 270.4 | 12.2 | 15.4 | 13.6 |
| 4. X-EMB1 (inclusion 3) | 780.0 | 273.1 | 10.3 | 14.6 | 13.8 |
| 5. X-EMB2 (inclusion 4) | 781.5 | 271.3 | 11.0 | 15.1 | 14.6 |
| 6. X-EMB2 (inclusion 5) | 783.3 | 271.6 | 11.1 | 15.1 | 13.8 |
| 7. X-EMB2 (inclusion 6) | 783.4 | 270.7 | 10.7 | 14.6 | 13.7 |
| 8. X-EMB3 (inclusion 7) | 784.4 | 272.1 | 10.5 | 15.4 | 14.9 |
| 9. X-EMB3 (inclusion 8) | 781.5 | 272.5 | 11.5 | 14.8 | 14.2 |
| 5% LSD | 9.4 | 9.2 | 1.3 | 1.0 | 0.9 |
| R-Square | 0.0754 | 0.0123 | 0.1560 | 0.1949 | 0.1185 |
| RMSE | 12.1 | 11.8 | 1.6 | 1.2 | 1.1 |
| Treat | 0.3843 | 0.9982 | 0.0106 | 0.0010 | 0.0711 |

Figure 4:
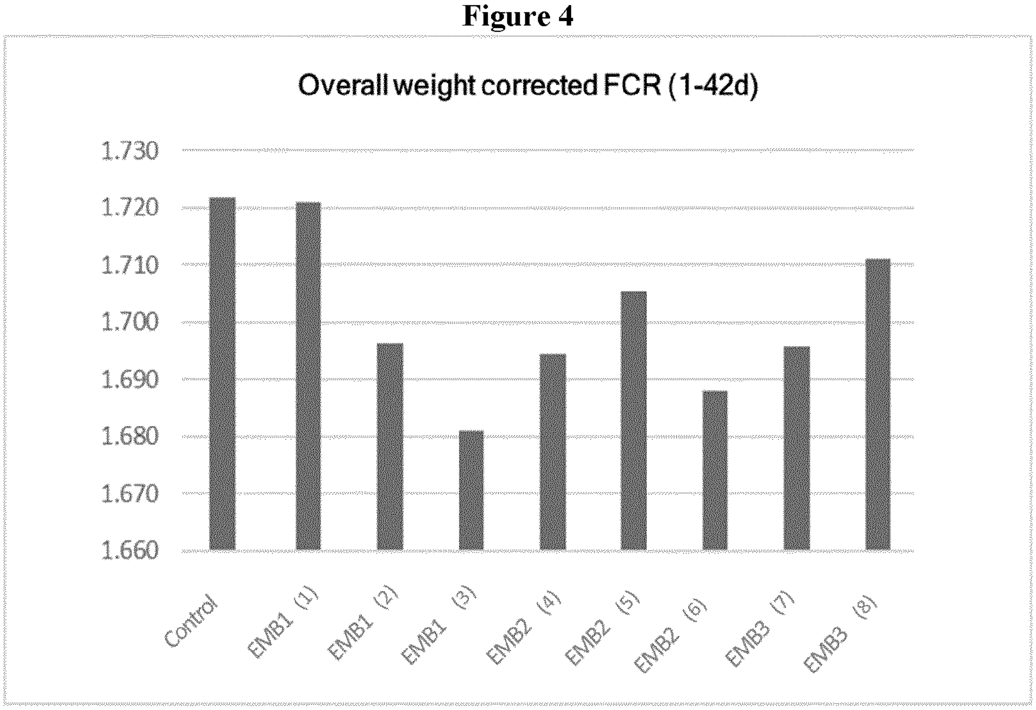
FIG. 4 shows overall weight corrected FCR for Day 1-42.

During the Day 1-42 (FIG. 4) no treatment effects were significant as per the model or treatment p values but some treatments did exceed the 5% confidence limits from one another. One example is overall weight corrected FCR as shown below where it appears that EMB1 (inclusion 3) treatments did in fact outperform the control.

In four additional trials similar to above, EMB1 in combination with a xylanase enzyme had the outstanding effect on poultry performance (see Table 8).

TABLE 8

| Poultry performance with EMB1 in combination with a xylanase enzyme | | | | | |
|---|---|---|---|---|---|
| | Overall weight corrected FCR | | | | |
| Trial | Control | Inclusion 9 | Inclusion 10 | Inclusion 11 | Inclusion 12 |
| 1 | 1.709 | | 1.719 | 1.672 | |
| 2 | 1.753 | | 1.736 | 1.698 | 1.72 |
| 3 | 1.595 | 1.496 | 1.473 | 1.501 | |
| 4 | 1.734 | 1.61 | 1.59 | 1.58 | |

The invention claimed is:

1. An animal feed additive-comprising in wt %:

Total oligosaccharides: 25% to 75%;

Proteins and/or protein hydrolysates: 5% to 55%;

Lipids: 0% to 5%;

Phenolic compounds: 0% to 55%;

Minerals: <10%;

Moisture: <10%;

wherein the oligosaccharides comprise:

Glucans: 3% to 40%, by weight of total oligosaccharides;

Xylans: 10% to 50%, by weight of total oligosaccharides;

Arabinans: 3% to 50%, by weight of total oligosaccharides;

Mannans: 0% to 30%, by weight of total oligosaccharides;

and wherein distribution of degree of polymerisation (DP) of said oligosaccharides is DP1: 1% to 30%;

DP2 to DP30: 70% to 100%;

and wherein the animal feed is obtained by:

contacting a biomass with a catalyst to form a reaction mixture, wherein the catalyst comprises one or more ionic polymers, an ionic polymer network, a solid-supported ionic polymer, or a polymer membrane incorporating the one or more ionic polymers;

degrading the biomass in the reaction mixture to produce a liquid phase and a solid phase, wherein the liquid phase includes the animal feed additive, and the solid phase includes residual biomass;

separating at least a portion of the liquid phase from the solid phase to produce an isolated liquid phase; and recovering the animal feed additive from the isolated liquid phase;

wherein the ionic polymer consists of a first monomer corresponding in structure to Formula I:

(Formula I)

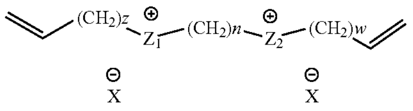

a second monomer corresponding in structure to Formula VI:

(Formula VI)

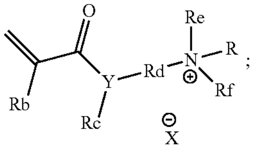

wherein n is selected from the group consisting of 1, 2, 3, 4, 5, and 6;

z and w are independently selected from the group consisting of zero, 1, 2, and 3;

$Z_1$ and $Z_2$ are cations each independently selected from the group consisting of:

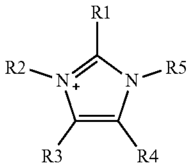

and

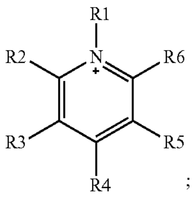

;

wherein R1, R2, R3, R4, R5, and R6 are each independently selected from the group consisting of a bond, H, $C_1$-$C_6$ alkyl, $C_1$-$C_6$ allyl, $CH_3$-$(CH_2)$p-O—$(CH_2)$q-$CH_3$, $C_1$-$C_6$ alkoxy, $C_1$-$C_6$ alkoxyalkyl, benzyl, —$SO_3H$, and —$(CH_2)$q-$SO_3H$, provided that two of R1, R2, R3, R4, R5, and R6 are each a bond;

p and q are independently selected from 0, 1, 2, 3, 4, 5, and 6;

$X^-$ is selected from the group consisting of $F^-$, $Cl^-$, $Br^-$, $I^-$, $ClO_4^-$, $BF_4^-$, $PF_6^-$, $AsF_6^-$, $SbF_6^-$, $NO_2^-$, $NO_3^-$, $HSO_4^-$, $SO_4^{2-}$, $PO_4^{3-}$, $HPO_4^{2-}$, $CF_3CO_2^-$, $CF_3CO_3^-$, $CO_3^{2-}$, $CF_3SO_3^-$, $C_1$-$C_6$ carboxylate, $CN^-$, $SCN^-$, $OCN^-$, $CNO^-$, $N_3^-$, tosylate, mesylate, trifluoromethanesulfonate, trifluoroethane sulfonate, di-trifluoromethanesulfonyl amino, docusate, and xylenesulfonate;

Rb and Rc are each independently selected from the group consisting of H and $CH_3$, or Rb and Rc are each independently absent;

Rd is $C_1$-$C_{24}$ alkylene or $C_1$-$C_{24}$ alkyl, optionally substituted by $C_1$-$C_{24}$ alkyl;

Re and Rf are each independently $C_1$-$C_{24}$ alkyl;

Y is N or O, provided that when Y is O, Rc is absent;

R is selected from the group consisting of $C_1$-$C_{24}$ alkyl and $C_5$-$C_{10}$ aryl, or R is absent;

wherein the ionic polymer network comprises the one or more ionic polymers cross-linked;

wherein the solid support has at least one surface comprising the one or more ionic polymers or the ionic polymer network;

wherein the polymer membrane incorporates the one or more ionic polymers or the ionic polymer network.

2. The animal feed additive of claim 1, wherein the animal feed additive is obtained further by:

determining the lipids, proteins and/or carbohydrates content in the biomass;

pre-treating the biomass; and/or removing the lipids and/or proteins from the biomass.

* * * * *